(12) United States Patent
Grayson et al.

(10) Patent No.: US 8,563,041 B2
(45) Date of Patent: Oct. 22, 2013

(54) THERAPEUTIC PARTICLES SUITABLE FOR PARENTERAL ADMINISTRATION AND METHODS OF MAKING AND USING SAME

(75) Inventors: Amy Grayson, Brookline, MA (US); Stephen E. Zale, Hopkinton, MA (US); David Dewitt, Allston, MA (US)

(73) Assignee: BIND Therapeutics, Inc., Cambridge, MA (US)

( * ) Notice: Subject to any disclaimer, the term of this patent is extended or adjusted under 35 U.S.C. 154(b) by 142 days.

(21) Appl. No.: 12/636,105

(22) Filed: Dec. 11, 2009

(65) Prior Publication Data

US 2010/0226986 A1    Sep. 9, 2010

Related U.S. Application Data

(60) Provisional application No. 61/122,046, filed on Dec. 12, 2008, provisional application No. 61/159,625, filed on Mar. 12, 2009, provisional application No. 61/240,433, filed on Sep. 8, 2009.

(51) Int. Cl.
*A61K 9/14* (2006.01)
*C07D 305/00* (2006.01)
*C07D 407/00* (2006.01)
*C07C 237/00* (2006.01)

(52) U.S. Cl.
USPC ........... 424/489; 549/510; 562/439; 568/817; 977/773

(58) Field of Classification Search
None
See application file for complete search history.

(56) References Cited

U.S. PATENT DOCUMENTS

| | | | |
|---|---|---|---|
| 5,302,401 A | 4/1994 | Liversidge et al. |
| 5,543,158 A | 8/1996 | Gref et al. |
| 5,578,325 A | 11/1996 | Domb et al. |
| 5,766,635 A | 6/1998 | Spenleuhauer et al. |
| 6,007,845 A | 12/1999 | Domb et al. |
| 6,136,846 A | 10/2000 | Rubinfeld et al. |
| 6,139,870 A | 10/2000 | Verrecchia |
| 6,201,072 B1 | 3/2001 | Rathi et al. |
| 6,254,890 B1 | 7/2001 | Hirosue et al. |
| 6,265,609 B1 | 7/2001 | Jackson et al. |
| 6,346,274 B1 | 2/2002 | Koll et al. |
| 6,395,718 B1 | 5/2002 | Slusher et al. |
| 6,528,499 B1 | 3/2003 | Kozikowski et al. |
| 6,841,547 B2 | 1/2005 | Brown et al. |
| 6,875,886 B2 | 4/2005 | Frangioni |
| 6,890,950 B2 | 5/2005 | Boothman et al. |
| 6,902,743 B1 | 6/2005 | Setterstrom et al. |
| 6,916,788 B2 | 7/2005 | Seo et al. |
| 7,422,902 B1 | 9/2008 | Wheeler et al. |
| 8,003,128 B2 | 8/2011 | Kreuter et al. |
| 8,034,765 B2 | 10/2011 | De et al. |
| 8,206,747 B2 | 6/2012 | Zale et al. |
| 8,211,473 B2 | 7/2012 | Troiano et al. |
| 2002/0045582 A1 | 4/2002 | Margolin et al. |
| 2002/0119916 A1 | 8/2002 | Hassan |
| 2003/0068377 A1 | 4/2003 | Fowers et al. |
| 2003/0143184 A1 | 7/2003 | Seo et al. |
| 2003/0232887 A1 | 12/2003 | Johnson et al. |
| 2003/0235619 A1 | 12/2003 | Allen et al. |
| 2004/0054190 A1 | 3/2004 | Pomper et al. |
| 2004/0071768 A1 | 4/2004 | Sarris et al. |
| 2004/0086544 A1 | 5/2004 | Bezemer et al. |
| 2004/0185170 A1 | 9/2004 | Chungi et al. |
| 2004/0219224 A1 | 11/2004 | Yakovlevsky et al. |
| 2004/0220081 A1 | 11/2004 | Kreitz et al. |
| 2004/0247624 A1 | 12/2004 | Unger et al. |
| 2004/0247680 A1 | 12/2004 | Farokhzad et al. |
| 2005/0037075 A1 | 2/2005 | Farokhzad et al. |
| 2005/0037086 A1 | 2/2005 | Tyo et al. |
| 2005/0136258 A1 | 6/2005 | Nie et al. |
| 2005/0142205 A1 | 6/2005 | Rashba-Step et al. |
| 2005/0256071 A1 | 11/2005 | Davis |
| 2005/0266067 A1 | 12/2005 | Sengupta et al. |
| 2006/0002852 A1 | 1/2006 | Saltzman et al. |
| 2006/0002971 A1 | 1/2006 | Saltzman et al. |
| 2006/0057219 A1 | 3/2006 | Nagasaki et al. |
| 2006/0110460 A1 | 5/2006 | Ferret et al. |
| 2006/0165987 A1 | 7/2006 | Hildgen et al. |
| 2007/0031402 A1 | 2/2007 | Zhang et al. |
| 2007/0041901 A1 | 2/2007 | Diener et al. |
| 2007/0043066 A1 | 2/2007 | Sum et al. |
| 2007/0053845 A1 | 3/2007 | Sengupta et al. |
| 2007/0154554 A1 | 7/2007 | Burgermeister et al. |
| 2008/0057102 A1 | 3/2008 | Roorda |
| 2008/0081074 A1 | 4/2008 | Gu et al. |
| 2008/0124400 A1 | 5/2008 | Liggins et al. |

(Continued)

FOREIGN PATENT DOCUMENTS

| | | |
|---|---|---|
| CN | 101053553 A | 10/2007 |
| EP | 0805678 A1 | 11/1997 |
| EP | 1985309 A1 | 10/2008 |
| EP | 2106806 A1 | 10/2009 |
| KR | 10-0418916 | 3/2002 |

(Continued)

OTHER PUBLICATIONS

Abizaid, Alexander et al., "Sirolimus-eluting stents inhibits neointimal hyperplasia in diabetic patients," European Heart Journal, 25, pp. 104-112 (2006).

(Continued)

*Primary Examiner* — Robert A Wax
*Assistant Examiner* — Jeffrey T Palenik
(74) *Attorney, Agent, or Firm* — Goodwin Procter LLP

(57) ABSTRACT

Disclosed herein are therapeutic compositions for treating and preventing diseases such as neointimal hyperplasia (NIH), where the compositions comprise a therapeutic particle that has a localized association with a blood vessel and a therapeutic agent, such as an anti-NIH agent. Methods of use of the therapeutic compositions are also disclosed.

4 Claims, 10 Drawing Sheets

(56) References Cited

U.S. PATENT DOCUMENTS

| | | |
|---|---|---|
| 2008/0193381 A1 | 8/2008 | Babich et al. |
| 2008/0267876 A1 | 10/2008 | Benita et al. |
| 2009/0053293 A1 | 2/2009 | Liang et al. |
| 2009/0053315 A1 | 2/2009 | Brough et al. |
| 2009/0061009 A1 | 3/2009 | Schwarz et al. |
| 2009/0061010 A1 | 3/2009 | Zale et al. |
| 2009/0074753 A1 | 3/2009 | Lynch |
| 2009/0074828 A1 | 3/2009 | Alexis et al. |
| 2009/0155349 A1 | 6/2009 | Heller et al. |
| 2009/0170753 A1 | 7/2009 | Welz et al. |
| 2009/0306120 A1 | 12/2009 | Lim et al. |
| 2009/0317479 A1 | 12/2009 | Ishihara et al. |
| 2010/0008998 A1 | 1/2010 | Kang et al. |
| 2010/0040537 A1 | 2/2010 | Gu et al. |
| 2010/0068285 A1 | 3/2010 | Zale et al. |
| 2010/0068286 A1 | 3/2010 | Troiano et al. |
| 2010/0069426 A1 | 3/2010 | Zale et al. |
| 2010/0087337 A1 | 4/2010 | Dewitt |
| 2010/0104645 A1 | 4/2010 | Ali et al. |
| 2010/0104655 A1 | 4/2010 | Zale et al. |
| 2010/0166866 A1 | 7/2010 | Fischer et al. |
| 2010/0216804 A1 | 8/2010 | Zale et al. |
| 2010/0226986 A1 | 9/2010 | Grayson et al. |
| 2010/0266491 A1 | 10/2010 | Farokhzad et al. |
| 2010/0303900 A1 | 12/2010 | Ramstack et al. |
| 2010/0316725 A1 | 12/2010 | Ryde et al. |
| 2011/0159079 A1 | 6/2011 | Li et al. |
| 2011/0217377 A1 | 9/2011 | Zale et al. |
| 2011/0224238 A1 | 9/2011 | Zale et al. |
| 2011/0274759 A1 | 11/2011 | Troiano et al. |
| 2011/0275704 A1 | 11/2011 | Troiano et al. |
| 2011/0294717 A1 | 12/2011 | Ali et al. |
| 2012/0004293 A1 | 1/2012 | Zale et al. |
| 2012/0027820 A1 | 2/2012 | Troiano et al. |
| 2012/0140790 A1 | 6/2012 | Ali et al. |

FOREIGN PATENT DOCUMENTS

| | | |
|---|---|---|
| KR | 20020041712 | 6/2002 |
| WO | WO-0000222 A1 | 1/2000 |
| WO | WO-03055469 A1 | 7/2003 |
| WO | WO-03/086369 A2 | 10/2003 |
| WO | WO-2004084871 A1 | 10/2004 |
| WO | WO-2005/046572 | 5/2005 |
| WO | WO-2006/093991 | 9/2006 |
| WO | WO-2007/024323 | 3/2007 |
| WO | WO-2007/028341 | 3/2007 |
| WO | WO-2007/034479 | 3/2007 |
| WO | WO-2007/074604 | 7/2007 |
| WO | WO-2007110152 A2 | 10/2007 |
| WO | WO-2007/133807 | 11/2007 |
| WO | WO-2008/019142 | 2/2008 |
| WO | WO-2008/058192 | 5/2008 |
| WO | WO-2008/105773 | 9/2008 |
| WO | WO-2008/121949 | 10/2008 |
| WO | WO-2008/124632 | 10/2008 |
| WO | WO-2008/124634 | 10/2008 |
| WO | WO-2008/124639 | 10/2008 |
| WO | WO-2008/139804 | 11/2008 |
| WO | WO-2009/070302 | 6/2009 |
| WO | WO-2010/005721 | 1/2010 |
| WO | WO-2010/005723 | 1/2010 |
| WO | WO-2010/005725 | 1/2010 |
| WO | WO-2010/005726 | 1/2010 |
| WO | WO-2010/068866 | 6/2010 |
| WO | WO-2010/075072 | 7/2010 |
| WO | WO-2010/114768 | 10/2010 |
| WO | WO-2010/114770 | 10/2010 |
| WO | WO-2011/072218 | 6/2011 |
| WO | WO-2011/084513 | 7/2011 |
| WO | WO-2011/084518 | 7/2011 |
| WO | WO-2011/084521 | 7/2011 |
| WO | WO-2011/119995 | 9/2011 |
| WO | WO-2012054923 A2 | 4/2012 |

OTHER PUBLICATIONS

Barinka, Cyril, et al., "Interactions Between Human Glutamate Carboxypeptidase II and Urea-Based Inhibitors: Structural Characterization," J. Med. Chem. 2008, 51, 7737-7743, pp. 7737-7743.

Barinka, Cyril, et al., Structural Insight into the Pharmacophore Pocket of Human Glutamate Carboxypeptidase II, J. Med. Chem. 2007, 50, pp. 3267-3273.

Blindt, Rudiger et al., "A novel drug-eluting stent coated with an integrin-binding cyclic Arg-Gly-Asp peptide inhibits neointimal hyperplasia by recruiting endothelial progenitor cells," Journal of the American College of Cardiology, 47(9), pp. 1786-1795 (2006).

Caliceti, P. et al., "Effective protein release form PEG/PLA nanoparticles produced by compressed gas anti-solvent precipitation techniques," Journal of Controlled Release, vol. 94, pp. 195-205 (2004).

Chandran, Sachin S., et al., "Characterization of a Targeted Nanoparticle Functionalized with a Urea-Based Inhibitor of Prostate-Specific Membrane Antigen (PSMA)," Cancer Biology & Therapy 7:4, pp. 1-9; Apr. 2008.

Chen, Ying, et al., "Radiohalogenated Prostate-Specific Membrane Antigen (PSMA)-Based Ureas as Imaging Agents for Prostate Cancer," J. Med. Chem., 2008, 51 (24), pp. 7933-7943.

Dancey, J.E. et al., "Therapeutic Targets" mTOR and Related Pathways, Cancer Biology & Therapy, 5:9, Sep. 2006, pp. 1065-1073.

De Jaeghere, F. et al., "Freeze-Drying and Lyopreservation of Diblock and Triblock Poly(Lactic Acid)-Poly(Ethylene Oxide) (PLA-PEO) Copolymer Nanoparticles," Pharmaceutical Development and Technology, vol. 5(4), 2000, pp. 473-483.

Farokhzad, Omid C., et al., "Nanoparticle-Aptamer Bioconjugates: A New Approach for Targeting Prostate Cancer Cells," Cancer Research 64, pp. 7668-7672, Nov. 1, 2004.

Farokhzad, Omid C., et al., "Targeted Nanoparticle-Aptamer Bioconjugates for Cancer Chemotherapy in vivo," PNAS (2006) 103:16, pp. 6315-6320.

Foss, Catherine A., et al., "Radiolabeled Small-Molecule Ligands for Prostate-Specific Membrane Antigen: In Vivo Imaging in Experimental Models of Prostate Cancer," Clin. Cancer Res. 2005;11(11), pp. 4022-4028.

Foss, Catherine, Poster Session: Novel Probes and Activation Strategies, Part 3, "Synthesis and Validation of a Novel Small-Molecule Fluorescent Probe for PSMA Expression in Human Tumor Neovasculature," 4th Annual Meeting for the Society for Molecular Imaging, Sep. 7-10, 2005.

Gao, Xiaohu et al., "In vivo cancer targeting and imaging with semiconductor quantum dots," Nature Biotechnology, vol. 22, No. 8, pp. 969-976 (2004).

Gref, Ruxandra, et al., "Biodegradable Long-Circulating Polymeric Nanospheres," Science, 1994, vol. 263, pp. 1600-1603.

Heald, CR et al., "Poly(lactic acid)-Poly(ethylene oxide) (PLA-PEG) Nanoparticles: NMR Studies of the Central Solidlike PLA Core and the Liquid PEG Corona," Langmuir, vol. 18, 2002, pp. 3669-3675.

Heldman, Alan et al., "Paclitaxel stent coating inhibits neointimal hyperplasia at 4 weeks in a porcine model of coronary restenosis," Circulation, 103, pp. 2289-2295 (2001).

Humblet, Valerie, et al., "An HPLC/Mass Spectrometry Platform for the Development of Multimodality Contrast Agents and Targeted Therapeutics: Prostate-Specific Membrane Antigen Small Molecule Derivatives," Contrast Med. Mol. Imaging 1: pp. 196-211 (2006).

Humblet, Valerie, et al., "High-Affinity Near-Infrared Fluorescent Small-Molecule Contrast Agents for In Vivo Imaging of Prostate-Specific Membrane Antigen," Molecular Imaging, vol. 4, Oct. 2005, pp. 448-462.

International Search Report for Application No. PCT/US08/13158 dated Jan. 20, 2009 and mailed Feb. 17, 2009.

International Search Report for Application No. PCT/US08/58873 dated Aug. 15, 2008 and mailed Aug. 28, 2008.

International Search Report for Application No. PCT/US09/47513 dated Jan. 18, 2010 and mailed Jan. 18, 2010.

International Search Report for PCT/US09/47515 dated Jan. 18, 2010 and mailed Jan. 19, 2010.

International Search Report for PCT/US09/47517 dated Feb. 25, 2010 and mailed Mar. 2, 2010.

(56) References Cited

OTHER PUBLICATIONS

International Search Report for PCT/US09/47518 dated Mar. 5, 2010 and mailed Mar. 5, 2010.
International Search Report for Application No. PCT/US09/67672 dated Aug. 20, 2010 and mailed Aug. 23, 2010.
International Search Report for Application No. PCT/US09/68028 dated Aug. 9, 2010 and mailed Aug. 23, 2010.
Jayaprakash, Sarva, et al., "Design and Synthesis of a PSMA Inhibitor-Doxorubicin Conjugate for Targeted Prostrate Cancer Therapy," ChemMedChem 2006, 1, pp. 299-302.
Jiang, X.Y. et al., "Preparation of PLA and PLGA Nanoparticles by Binary Organic Solvent Diffusion Method," J. Cent. South Univ. Technol., vol. 10, No. 3, Sep. 2003, pp. 202-206.
Kozikowski, Alan P., et al., Design of Remarkably Simple, Yet Potent Urea-Based Inhibitors of Glutamate Carboxypeptidase II (NAALADase), J. Med. Chem, 2001, 44, pp. 298-301.
Kozikowski, Alan P., et al., "Synthesis of Urea-Based Inhibitors as Active Site Probes of Glutamate Carboxypeptidase II: Efficacy as Analgesic Agents," J. Med. Chem. 2004, 47, pp. 1729-1738.
Maresca, K.P., et al., "A Series of Halogenated Heterodimeric Inhibitors of Prostate Specific Membrane Antigen (PSMA) as Radiolabeled Probes for Targeting Prostate Cancer," J. Med. Chem. (2009) 52(2):347-57.
Mease, Ronnie C., et al., "N-[N-[(S)-1,3-Dicarboxypropyl]Carbamoyl]-4-[$^{18}$F] Fluorobenzyl-L-Cysteine, [$^{18}$F] DCFBC: A New Imaging Probe for Prostate Cancer," Clin. Cancer Res. 2008;14(10) May 15, 2008, pp. 3036-3043.
Misra, Preeti, et al., "Production of Multimeric Prostate-Specific Membrance Antigen Small-Molecule Radiotracers Using a Solid-Phase 99m Tc Preloading Strategy," The Journal of Nuclear Medicine, vol. 48, No. 8, pp. 1379-1389., Aug. 2007.
Oliver, A. Jayne, et al., "Conformational and SAR Analysis of NAALADase and PSMA Inhibitors," Biorganic & Medicinal Chemistry 11 (2003) pp. 4455-4461.
Pomper, Martin G., Russell H. Morgan Department of Radiology and Radiological Science, Johns Hopkins University, "New Developments in Molecular Imaging of Prostate Cancer," Topical Symposium on: Advanced Molecular Imaging Techniques in the Detection, Diagnosis, Therapy, and Follow-up of Prostate Cancer, Palazzo Barberini, Rome, Dec. 6, 2005.
Sapra, P. et al., "Ligand-targeted liposomal anticancer drugs," PERGAMON, Progress in Lipid Research, vol. 42, pp. 439-462 (2003).
Tang, Hailun, et al., "Prostate Targeting Ligands Based on N-Acetylated α-Linked Acidic Dipeptidase," Biochemical and Biophysical Research Communications 307 (2003), pp. 8-14.
Tobio, M. et al., "Stealth PLA-PEG Nanoparticles as Protein Carriers for Nasal Administration," Pharmaceutical Research, vol. 15, No. 2, 1998, pp. 270-275.
Yamamoto, Y. et al., "Long-circulating poly(ehtylene glycol)-poly(D,L-lactide) block copolymer micelles with modulated surface charge," Journal of Controlled Release, vol. 77, pp. 27-38 (2001).
Zhang, Qi et al., "Neointimal hyperplasia persists at six months after siroli mus-eluting stent implantation in diabetic porcine," Cardiovascular Diabetology, 6(16), pp. 1-7 (2007).
Zhou, Jia, et al., "NAAG Peptidase Inhibitors and Their Potential for Diagnosis and Therapy," Nature Reviews/Drug Discovery, vol. 4, Dec. 2005, pp. 1015-1026.
Abdelwahed et al., "Freeze-Drying of Nanoparticles: Formulation, Process and Storage Considerations," Adv. Drug Deliv. Rev. (2006) 58:1688-1713.
Adams et al., "Amphiphillic Block Copolymers for Drug Delivery," J. Pharm. Sci. (2003) 92:1343-1355.
Cheng et al., "Formulation of Functionalized PLGA-PEG Nanoparticles for in Vivo Targeted Drug Delivery," Biomaterials (2007) 28:869-879.
Davaran et al. "Preparation and in vitro Evaluation of Linear and Star-branched PLGA Nanoparticles for Insulin Delivery," J. Bioact. Compat. Polym. (2008) 28:115-131.

De Jaeghere et al., "Formulation and Lyoprotection of Poly (Lactic Acid-Co-Ethylene Oxide) Nanoparticles: Influence on Physical Stability and In Vitro Cell Uptake," Pharm. Res. (1999) 16:859-866.
Eurasian Search Report for Application No. EA 201170038, dated Jul. 8, 2011.
Ewesuedo et al., "Chapter 1: Systemically Administrated Drugs." Drug delivery systems in cancer therapy. Ed. D.M. Brown. Totowa:Humana, 2003, pp. 3-14.
Extended European Search Report for Application No. EP 09794913.5, mailed Jul. 8, 2011.
Govender et al., "Defining the Drug Incorporation Properties of PLA-PEG Nanoparticles," Int. J. Pharm. (2000) 199:95-110.
Gref et al. "Development and Chracterization of CyA-loaded Poly(lactic acid)-poly(ethylene glycol)PEG Micro- and Nanoparticles. Comparision with Conventional PLA Particluate Carriers," Eur. J. Pharm. Biopharm. (2001) 51:111-118.
Gu et al., "Precise Engineering of Targeted Nanoparticles by Using Self-Assembled Biointegrated Block Copolymers," Proc. Natl. Acad. Sci. USA (2008) 105:2586-2591.
Hederstrom et al. "Purification and Surface Modification of Polymeric Nanoparticles for Medical Applications." Master's thesis. SINTEF Materials and Chemistry, Trondheim, Norway, Mar. 3, 2008.
International Search Report for Application No. PCT/US10/59879 dated Aug. 30, 2011 and mailed Aug. 30, 2011.
International Search Report for Application No. PCT/US10/60564 dated Sep. 29, 2011 and mailed Sep. 29, 2011.
International Search Report for Application No. PCT/US10/60570 dated Aug. 25, 2011 and mailed Aug. 25, 2011.
International Search Report for Application No. PCT/US10/60575 dated Aug. 25, 2011 and mailed Aug. 25, 2011.
Koziara et al., "Blood Compatibility of Cetyl Alcohol/Polysorbate-Based Nanoparticles," Pharm. Res. (2005) 22(11):1821-1828.
Kwon et al., "Long Acting Porous Microparticle for Pulmonary Protein Delivery," Inter. J. Pharm. (2007) 333:5-9.
Murugesan, S. et al., "Pegylated Poly(lactide-co-glycolidel (PLGA) Nanoparticulate Delievery of Docetaxel: Synthesis of Diblock Copolymers, Optimization of Preparation Variables on Formulation Characteristics and in Vitro Release Studies," J. Biomed. Nanotechnol. (2007) 3:52-60.
Musumeci et al., "Lyoprotected Nanosphere Formulations for Paclitaxel Controlled Delivery," J. Nanosci. Nanotechnol. (2006) 6:1-8.
Ojer et al., "Spray-Drying of Poly(anhydride) Nanoparticles for Drug/Antigen Delivery " J. Drug Del. Sci. Tech., (2010) 20:353-359.
Omelczuk et al. "The Influence of Polymer Glass Transition Temperature and Molecular Weight on Drug Release from Tablets Containing Poly(DL-lactic acid)," Pharm. Res. (1992) 9(1):26-32.
Pourcelle et al., "PCL-PEG-Based Nanoparticles Grafted with GRGDS Peptide: Preparation and Surface Analysis by XPS," Biomacromolecules (2007) 8:3977-3983.
Pulkkinen et al. "Three-Step Tumor Targeting of Paclitaxel Using Biotinylated PLA-PEG Nanoparticles and Avidin-Biotin Technology: Formulation Development and In Vitro Anticancer Activity," Eur. J. Pharm. Biopharm. (2008) 70:66-74.
Riley et al., "Colloidal Stability and Drug Incorporation Aspects of Micellar-Like PLA-PEG Nanoparticles," Colloids Surf. B: Biointer. (1999) 16:147-59.
Sweetman, "Martindale: The Complete Drug Reference," 33rd ed., 2002, Pharmaceutical Press, entry for Docetaxel, p. 534.
Tamilvanan et al., "Manufacturing Techniques and Excipients Used During the Design of Biodegradable Polymer-based Microspheres Containing Therapeutic Peptide/Protein for Parenteral Controlled Drug Delivery, " PDA J. Pharm. Sci. Technol. (2008) 62:125-154.
Vicari et al., "Paclitaxel Loading in PLGA Nanospheres Affected the in Vitro Drug Cell Accumulation and Antiproliferative Activity," BMC Cancer (2008) 8:212.
Extended European Search Report for Application No. EP 09794915.0, mailed Jan. 25, 2012.
Bilati et al., "Nanoprecipitation Versus Emulsion-based Techniques for the Encapsulation of Proteins into Biodegradable Nanoparticles and Process-related Stability Issues," AAPS PharmSciTech. (2005) 6(4):E594-E604.

(56) References Cited

OTHER PUBLICATIONS

Eurasian Search Report for Application No. EA 201170039, dated Nov. 21, 2011.

Extended European Search Report for Application No. EP 09835578.7, mailed May 18, 2012.

Feng et al., "Nanoparticles of Biodegradable Polymers for Clinical Administration of Paclitaxel," *Curr. Med. Chem.* (2004) 11:413-424.

Fournier et al., "Experimental Studies and Preliminary Clinical Trial of Vinorelbine-loaded Polymeric Bioresorbable Implants for the Local Treatment of Solid Tumors " *Cancer Res.* (1991) 51: 5384-5391.

Hrkach et al., "Preclinical Development and Clinical Translation of a PSMA-Targeted Docetaxel Nanoparticle with a Differentiated Pharmacological Profile," *Sci. Transl. Med.* (2012) 4:1-11.

International Search Report for Application No. PCT/US11/057498 dated May 9, 2012 and mailed May 10, 2012.

Lyseng-Williamson et al. "Docetaxel a Review of its Use in Metastatic Breast Cancer," *Drugs.* (2005) 65(17):2513-16.

Murugesan et al., "Long circulating PEGylated poly(D,L-lactide-co-glycolide) nanoparticle delivery of Docetaxel to solid tumors," *J. Drug Target.* (2008) 16(5):424-435.

Musumeci et al., "PLA/PLGA Nanoparticles for Sustained Release of Docetaxel " *Int. J. Pharm.* (2006) 325:172-179.

Olivier, "Drug Transport to Brain with Targeted Nanoparticles," *NeuroTherapeutics* (2005) 2:108-119.

Gill et al., "Modulated Differential Scanning Calorimetry " *J. Thermal Analysis.* (1993) 40:931-939.

Peracchia et al., "PEG-coated nanospheres from amphiphilic diblock and multiblock copolymers: Investigation of their drug encapsulation and release characteristics," *J. of Controlled Release.* (1996) 46:223-231.

THERAPEUTIC PARTICLES SUITABLE FOR PARENTERAL ADMINISTRATION AND METHODS OF MAKING AND USING SAME

RELATED APPLICATIONS

This application claims priority to U.S. Ser. No. 61/122, 046, filed Dec. 12, 2008, U.S. Ser. No. 61/159,625, filed Mar. 12, 2009, and U.S. Ser. No. 61/240,433 filed Sep. 8, 2009, each of which is hereby incorporated by reference in its entirety.

BACKGROUND

The process of restonosis, or renarrowing of an e.g. a coronary artery lumen following a revascularization procedure, most likely begins at the time of percutaneous intervention. Restenosis typically can involve mechanical processes such as elastic recoil, or acute renarrowing of an artery after e.g. balloon angioplasty, and processes such as negative arterial remodeling—as the vessel begins to heat, the outermost vessel layer (the adventitial layer) may shrink inward. Neointimal hyperplasia (NIH), another process in the development of restenosis, is not a mechanical function of the anatomy of an artery, but a biological wound healing response to the injury caused by percutaneous coronary intervention. Neointimal hyperplasia can involve smooth muscle cell proliferation, migrations and/or production of the extracellular matrix. With the introduction of arterial stents, the problems of elastic recoil or negative arterial remodeling has been substantially eliminated. However, neointimal hyperplasia is still a primary cause of restenosis after the introduction of a stent in the artery of a patient. Both bare metal stents and drug-eluting stents that typically elute an anti-restenosis agent are available.

Drug eluting stents are not optimal under all conditions, however. Such stents may not be appropriate for small vessels, and drug eluting stents can hinder vessel healing. For example, drug eluting stents may lead to a higher rate of thrombosis e.g. a year after implantation, when for example antiplatelet therapy (e.g. clopidogrel) is discontinued. For patients needing surgery, for example, patients may suffer fatal heart attacks due to clotting inside of drug-eluting stents, even months or years after surgery, particular if blood thinning medication is stopped (as is often necessary) before surgery. Patients identified as being likely to be non-compliant with antiplatelet therapy may not be suitable candidates for drug-eluting stents.

Therefore, it has been suggested that use of bare metal stents may actually provide a safer choice, at least for some patients. Improved compositions and methods for delivery of anti-neointimal hyperplasia, or anti-restenosis, agents for local and/or targeted delivery to blood vessels, for example, in conjunction with placement of a bare-metal stents is therefore needed.

SUMMARY

This disclosure is generally directed to therapeutic compositions that include therapeutic particles comprising an anti-neointimal hyperplasia (NIH) agent. Such therapeutic particles may be capable of releasing said anti-NIH agent to a blood vessel, for example, to a basement vascular membrane of a blood vessel. For example, such particles may be capable of releasing an anti-NIH agent for at least about 8 hours when a disclosed therapeutic particle or composition is placed in the blood vessel. Such compositions may be used, for example, with a patient receiving a vascular stent, e.g. a bare metal stent, in a blood vessel.

For example, the disclosure provides a therapeutic composition comprising a plurality of therapeutic particles each comprising an anti-NIH agent and a basement vascular membrane targeting peptide, wherein a single administration of a dose of the composition to a blood vessel is capable of contacting a blood vessel with a substantially higher surface area density as compared to a surface area density of a blood vessel contacted by a stent comprising the anti-NIH agent.

In an embodiment, the disclosure provides a method of preventing or deterring NIH in a blood vessel of a patient receiving a bare metal stent in a lesion of said blood vessel, comprising administering a composition comprising therapeutic particles, wherein said therapeutic particles comprise a basement vascular membrane targeting peptide and an anti-NIH agent. In some embodiments, methods disclosed herein include intravenous (e.g., systemic) administration of disclosed compositions and/or particles.

Also provided herein, in an embodiment, is a method of preventing or deterring NIH in a damaged blood vessel of a patient, comprising administering to said patient a therapeutic composition comprising a therapeutic particle, wherein said therapeutic particle may comprise a basement vascular membrane targeting peptide and an anti-NIH agent, and wherein said therapeutic particle substantially biodegrades after delivery of the anti-NIH agent thereby promoting healing of the blood vessel after said therapeutic particle has biodegraded.

Therapeutic compositions are provided herein, for example, for use in a patient receiving a vascular stent, comprising about 1 to about 20 mole percent targeting co-polymer wherein the targeting co-polymer is chosen from: a) PLA-PEG-basement vascular membrane targeting peptide; b) poly (lactic) acid—co poly (glycolic) acid-PEG-basement vascular membrane targeting peptide; c) DSPE-PEG-basement vascular membrane targeting peptide; and about 0.2 to about 30 weight percent anti-neointimal hyperplasia (NIH) agent (e.g. paclitaxel); about 50 to about 90 weight percent non-targeted polylactic acid or poly-lactic acid-PEG. For example, such a targeting co-polymer may include PLA-PEG, wherein for example poly(lactic acid) has a number average molecular weight of about 15 to 20 kDa and/or poly(ethylene) glycol has a number average molecular weight of about 4 to about 6 kDa. Contemplated basement vascular membrane targeting peptides may be selected, for example, from: CREKA (SEQ ID NO: 1) or CARLYQKLN (SEQ ID NO: 2).

BRIEF DESCRIPTION OF THE FIGURES

FIG. 1A illustrates delivery by guide catheter in the blood flow. FIG. 1B illustrates use of a balloon catheter for proximal delivery. FIG. 1C illustrates the use of a guide catheter with a balloon catheter for distal delivery.

DETAILED DESCRIPTION

Figure 1:
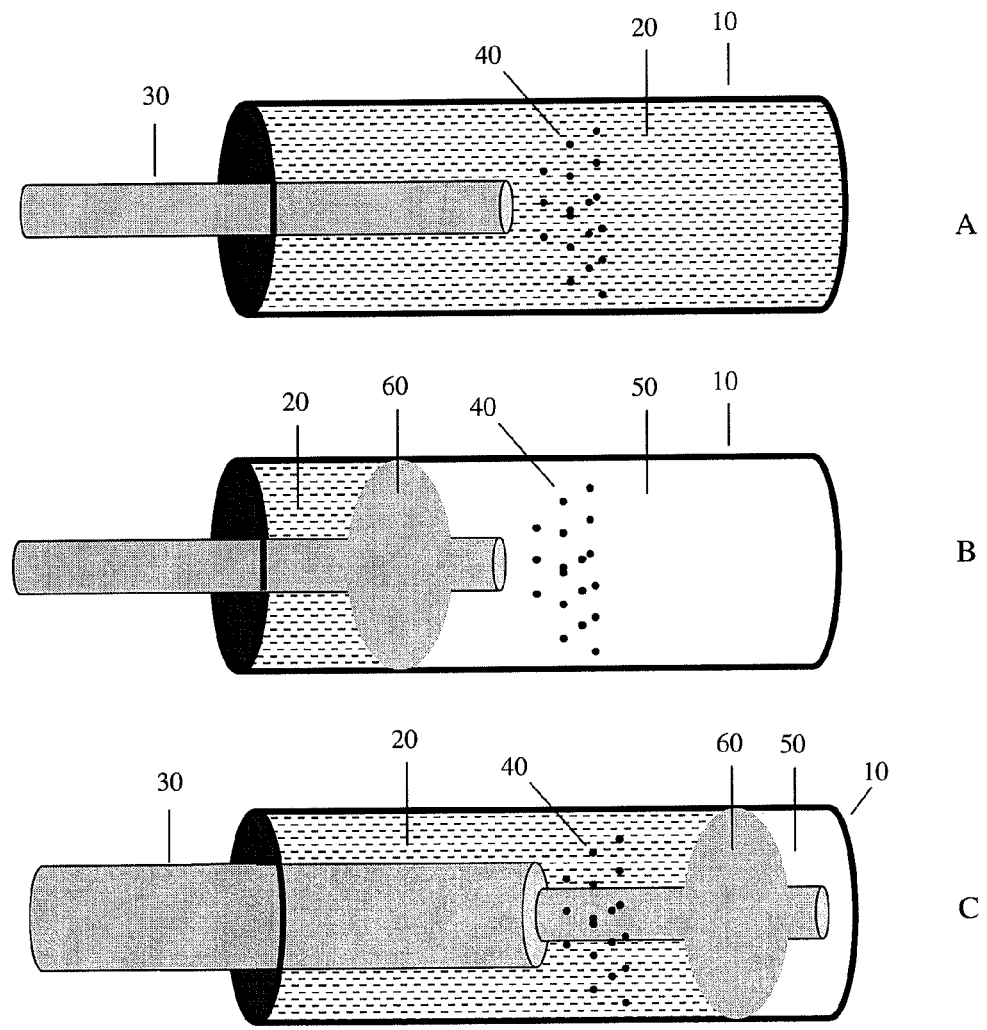
FIG. 1 depicts three methods for delivery of compositions of the invention to a target site in a blood vessel, where the blood flow 20 is from left to right in the diagram.

The features and other details of the disclosure will now be more particularly described. Before further description of the present invention, certain terms employed in the specification, examples and appended claims are collected here. These definitions should be read in light of the remainder of the disclosure and understood as by a person of skill in the art. Unless defined otherwise, all technical and scientific terms used herein have the same meaning as commonly understood by a person of ordinary skill in the art.

Definitions

"Treating" includes any effect, e.g., lessening, reducing, modulating, or eliminating, that results in the improvement of the condition, disease, disorder and the like.

"Pharmaceutically or pharmacologically acceptable" include molecular entities and compositions that do not produce an adverse, allergic or other untoward reaction when administered to an animal, or a human, as appropriate. For human administration, preparations should meet sterility, pyrogenicity, general safety and purity standards as required by FDA Office of Biologics standards.

The term "pharmaceutically acceptable carrier" or "pharmaceutically acceptable excipient" as used herein refers to any and all solvents, dispersion media, coatings, isotonic and absorption delaying agents, and the like, that are compatible with pharmaceutical administration. The use of such media and agents for pharmaceutically active substances is well known in the art. The compositions may also contain other active compounds providing supplemental, additional, or enhanced therapeutic functions.

"Individual," "patient," or "subject" are used interchangeably and include any animal, including mammals, such as mice, rats, other rodents, rabbits, dogs, cats, swine, cattle, sheep, horses, or primates, and most preferably humans. The compounds and compositions of the invention can be administered to a mammal, such as a human, but can also be other mammals such as an animal in need of veterinary treatment, e.g., domestic animals (e.g., dogs, cats, and the like), farm animals (e.g., cows, sheep, pigs, horses, and the like) and laboratory animals (e.g., rats, mice, guinea pigs, and the like). The mammal treated in the methods of the invention is desirably a mammal in whom modulation of NIH is desired. "Modulation" includes antagonism (e.g., inhibition), agonism, partial antagonism and/or partial agonism.

In the present specification, the term "therapeutically effective amount" means the amount of the subject compound or composition that will elicit the biological or medical response of a tissue, system, animal or human that is being sought by the researcher, veterinarian, medical doctor or other clinician. The compounds and compositions of the invention are administered in therapeutically effective amounts to treat a disease. Alternatively, a therapeutically effective amount of a compound is the quantity required to achieve a desired therapeutic and/or prophylactic effect, such as an amount which results in the prevention of or a decrease in the symptoms associated with NIH.

The term "pharmaceutically acceptable salt(s)" as used herein refers to salts of acidic or basic groups that may be present in compounds used in the present compositions. Compounds included in the present compositions that are basic in nature are capable of forming a wide variety of salts with various inorganic and organic acids. The acids that may be used to prepare pharmaceutically acceptable acid addition salts of such basic compounds are those that form non-toxic acid addition salts, i.e., salts containing pharmacologically acceptable anions, including but not limited to malate, oxalate, chloride, bromide, iodide, nitrate, sulfate, bisulfate, phosphate, acid phosphate, isonicotinate, acetate, lactate, salicylate, citrate, tartrate, oleate, tannate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate and pamoate (i.e., 1,1'-methylene-bis-(2-hydroxy-3-naphthoate)) salts. Compounds included in the present compositions that include an amino moiety may form pharmaceutically acceptable salts with various amino acids, in addition to the acids mentioned above. Compounds included in the present compositions that are acidic in nature are capable of forming base salts with various pharmacologically acceptable cations. Examples of such salts include alkali metal or alkaline earth metal salts, such as calcium, magnesium, sodium, lithium, zinc, potassium, and iron salts.

This disclosure provides, at least in part, therapeutic compositions that include a therapeutic particle. Such therapeutic particles can include for example an anti-neointimal hyperplasia (NIH) agent or antiflammatory agent, and may be capable of releasing the anti-NIH agent to a vascular membrane of a blood vessel for at least about 2, 4, 6, 8, 10, 12, or even 24 or more hours, or 1, 2 or 3 or more days, or for about 1, 2, 4 or even 12 or more weeks, when the therapeutic particle is placed in the blood vessel. In some embodiments, a disclosed therapeutic particle may include basement vascular membrane targeting peptide.

In some embodiments, disclosed therapeutic compositions may be for use, e.g., administered to or with a patient receiving a stent such as a vascular stent, for example, a bare metal stent, or, in some embodiments, a drug-eluting stent. In an embodiment, disclosed compositions may release substantially equal or substantially more effective amount of the anti-NIH agent when placed in the blood vessel as compared to the amount released by a stent comprising the same anti-NIH agent if placed in the blood vessel. In some embodiments, a disclosed therapeutic composition may release about 10% to about 50% or more, e.g., about 40%, or about 30% of the anti-NIH agent initially, with a more controlled release of the remaining drug over time.

In one embodiment, the anti-NIH agent can be chosen from paclitaxel, sirolimus, zotarolimus and/or everolimus. For example, a disclosed therapeutic particle may comprise paclitaxel such that the therapeutic composition releases about 50 µg to about 1000 µg, about 50 µg to about 600 µg, or about 100 µg to about 300 µg, of paclitaxel to a target of interest, e.g. the basement vascular membrane. Such release can occur over a period of about 8 hours to about 8 weeks, such as about 8 hours to about 4 weeks, further such as about 8 hours to about 1 week. In another exemplary embodiment, a disclosed therapeutic particle may comprise sirolimus such that the therapeutic composition releases about 50 µg to about 250 µg, such as 50 µg to about 100 µg, about 75 µg to about 150 µg, of sirolimus to, e.g., the basement vascular membrane. A therapeutic particle may comprise zotarolimus, for example, such that the therapeutic composition releases about 50 μg to about 300 μg, such as about 50 μg to about 250 μg, or about 75 μg to about 150 μg, of zotarolimus to e.g., a basement vascular membrane. In another embodiment, the therapeutic particle may comprise everolimus, for example, such that the therapeutic composition releases about 50 μg to about 300 μg, such as about 50 μg to about 250 μg, further such as about 75 μg to about 150 μg, of everolimus to the basement vascular membrane. The release of such drugs can occur over a period of about 8 hours to about 8 weeks, such as about 8 hours to about 4 weeks, further such as about 8 hours to about 1 week.

Therapeutic particles disclosed herein may include about 5% to about 85% by weight of the anti-NIH agent, such as about 2% to about 35%, or about 10% to about 25%, e.g. about 10%, 15%, or 20% by weight. The therapeutic particle may be substantially biodegraded after about 1 month, after about 1 week, such as about 3 days, further such as about 1 day, after placement in the blood vessel.

In some embodiments, disclosed compositions may provide a decreased or substantially comparable NIH rate in the patient about 4 weeks, or 3 weeks, or 2 weeks, such as about 1 week, after receiving the vascular stent as compared to the NIH rate obtained by administration of a vascular stent alone. In another embodiment, the NIH rate may be decreased compared to that from administration of a vascular stent, e.g. a bare metal stent, alone.

Also provided herein are therapeutic compositions that include a plurality of therapeutic particles each comprising an anti-NIH agent and optionally, a basement vascular membrane targeting peptide, wherein a single administration of a dose of the composition to a blood vessel can be capable of contacting a blood vessel with a substantially higher surface area density as compared to a surface area density of a blood vessel, e.g a surface area density of endothelial cells, as compared to the surface area density contacted by a stent comprising the anti-NIH agent. In some embodiments, one or more doses of the composition, when administered, may contact the blood vessel with a substantially higher surface area density as compared to the density of blood vessel contacted by a stent that includes the anti-NIH agent. For example, compositions may contact least a surface area density of about least about 2%, such as at least 5%, such as at least 10% higher than the density of blood vessel contacted by a stent comprising the same or different anti-NIH agent, e.g. a drug-eluting stent.

Doses of disclosed compositions may be capable of delivering the anti-NIH agent to the blood vessel such that the concentration of the anti-NIH agent in the blood vessel tissue can be about 2 ng/mg to about 100 ng/mg, such as about 15 ng/mg to 50 ng/mg, further such as about 20 ng/mg to 40 ng/mg about 2 days after administration.

Another embodiment provides therapeutic compositions, e.g., for use in a patient receiving a vascular stent, comprising a plurality of first therapeutic particles, wherein the first therapeutic particles may be capable of localized association with a blood vessel structure, e.g. a basement membrane, smooth muscle cells, endothelial cells, extracellular matrix, or inner elastic lamina, and comprise a first therapeutic agent, e.g. an anti-NIH agent, and wherein a single administration of a dose of the composition to the blood vessel provides a faster endothelial cell healing rate at about 6 months, 4 months, or about 2 months, as compared to the endothelial healing rate of a patient receiving a stent comprising the first therapeutic agent at about 6 months. In another embodiment, a single administration (or multiple administrations) of a dose of a composition associates with a greater surface area density of the blood vessel structure as compared to a patient receiving a stent comprising the first therapeutic agent. Such compositions may further include a plurality of second therapeutic particles. The second therapeutic particles may be capable of localized association with a different blood vessel structure than the first therapeutic particles. The second therapeutic particles may comprise a second therapeutic agent, which may be different than the first therapeutic agent.

Also provided herein are therapeutic compositions that include a plurality of first therapeutic particles, wherein the first therapeutic particles may be capable of localized association with a blood vessel structure and comprise a first therapeutic agent such as an anti-NIH agent or anti-inflammatory agent; and a plurality of second therapeutic particles comprising a second therapeutic agent. In one embodiment, the plurality of first therapeutic particles can be present in a different amount than the plurality of second therapeutic particles. In another embodiment, the composition can comprise an equal amount of first and second therapeutic particles. A target of the first therapeutic agent may be different than a target of the second therapeutic agent. Such compositions may release a substantially equal or substantially greater amount of first therapeutic agent than second therapeutic agent, e.g. another anti-NIH agent or anti-inflammatory, in the blood vessel.

Exemplary second therapeutic agents include, but are not limited to, everolimus, paclitaxel, zotarolimus, pioglitazone, BO-653, rosiglitazone, sirolimus, dexamethasone, rapamycin, tacrolimus, biophosphonates, estrogen, angiopeptin, statin, PDGF inhibitors, ROCK inhibitors, MMP inhibitors, 2-CdA, corticosteroids, including combinations of zotarolimus and dexamethasone, nicotine, hydroxy-methylglutaryl coenzyme A (HMG CoA) reductase inhibitors, statins, niacin, bile acid resins, fibrates, antioxidants, nitric oxide generators, nitric oxide, extracellular matrix synthesis promoters, inhibitors of plaque inflammation, and extracellular degradation, and antithrombotic agents suchs as clopidogrel.

Contemplated anti-inflammatories or anti-inflammatory agents, which may be useful for restenosis, (e.g. vessel remodeling that occurs in restenosis starts with inflammation in response to the injury caused by angioplasty, and stopping this inflammation has been showed in animal studies to prevent restenosis), include sirolimus, corticosteroids (dexamethasone, prednisolone, triamcinolone acetonide, mometasone, amcinonide, budesonide, acetaminophen, NSAIDS, cox-2 inhibitors, and/or betamethasone.

Methods contemplated herein include, for example, a method of preventing or deterring NIH in a blood vessel of a patient receiving a bare metal stent in a lesion of the blood vessel, comprising administering a composition comprising disclosed therapeutic particles, such as therapeutic particles that may include a basement vascular membrane targeting peptide and an anti-NIH agent or anti-inflammatory. Disclosed methods may provides for decreased or substantially comparable NIH rate at about 2 weeks, such as about 1 week, after receiving the bare metal stent as compared to a patient receiving a stent comprising an anti-NIH agent at about 2 weeks or at about 1 week. In some embodiments, methods are provided that include administering or placing a bare metal stent in a blood vessel, and administering a disclosed therapeutic particle or composition before, after, or substantially simultaneously with the placement of the stent. The blood vessel receiving the stent may be less than about 2 mm in length, or between about 2 mm and about 3 mm in length, or may be greater than 3 mm in length. A treated blood vessel may be bifurcated or substantially non-bifurcated.

Such stents for use in the contemplated methods may be a thick or thin strut stent. For example, stents may be less than about 14 mm, such as less than about 10 mm, further such as less than about 7 mm in length. In another embodiment, contemplated stents may be about 14 mm to about 30 mm, such as about 17 mm to about 27 mm, further such as about 20 mm to about 25 mm in length.

In some embodiments, a patient being treated or contemplating treatment, may be intolerant or adverse to a particular medication, such as aspirin or clopidogrel. Patient populations suitable for treatment with disclosed methods include patients at risk of future surgery, e.g., cardiac or non-cardiac surgery.

Contemplated compositions or particles may be administered substantially simultaneously when a patient receives the stent and/or may be administered before or after the patient receives the stent. For example, compositions and/or particles may be introduced before or after the introduction of a balloon catheter into the blood vessel. The composition may be administered with the same delivery device used to deliver the stent to the patient, or a different delivery device. In one embodiment, the composition may be administered using a catheter, and/or may be administered intravenously. Disclosed compositions may be administered to a patient undergoing, for example, a coronary angioplasty, a peripheral angioplasty, a renal artery angioplasty, or a carotid angioplasty.

Another embodiment provides a method of preventing or deterring NIH in a damaged blood vessel of a patient, comprising administering to the patient a therapeutic composition comprising a therapeutic particle, wherein the therapeutic particle comprises a basement vascular membrane targeting peptide and an anti-NIH agent, and wherein the therapeutic particle substantially biodegrades after delivery of the anti-NIH agent thereby promoting healing of the blood vessel after the therapeutic particle has biodegraded. For example, a therapeutic particle may have substantially degraded about 1 day, such as about 1 week, further such as about 1 month after administration. The damaged blood vessel may have been caused by, for example, an implantation of a stent (e.g., a bare metal stent), a balloon angioplasty, or peripheral artery disease. In an exemplary embodiment, a damaged blood vessel may be caused, for example, by balloon angioplasty alone. Such methods may be suitable for patients where placement or administration of a stent (e.g. a bare metal stent or a drug eluting stent) is not appropriate, for example, patients suffering from superficial femoropopliteal artery obstructions or occlusions. After administration of disclosed particles or compositions, a blood vessel, may, in some embodiments, have substantially less risk of developing a thrombosis at about 1 month, or greater than about 1 month, about 2 months, further such as greater than about 3 months after administration as compared to a damaged blood vessel receiving a stent comprising an anti-NIH agent, e.g., a drug-eluting stent.

Therapeutic particles disclosed herein typically include a polymeric matrix. In one embodiment, the polymeric matrix comprises one, two or more synthetic or natural polymers. The term "polymer," as used herein, is given its ordinary meaning as used in the art, i.e., a molecular structure comprising one or more repeat units (monomers), connected by covalent bonds. The repeat units may all be identical, or in some cases, there may be more than one type of repeat unit present within the polymer. In some cases, the polymer can be biologically derived, i.e., a biopolymer. Non-limiting examples include peptides or proteins. In some cases, additional moieties may also be present in the polymer, for example biological moieties such as those described below. If more than one type of repeat unit is present within the polymer, then the polymer is said to be a "copolymer." It is to be understood that in any embodiment employing a polymer, the polymer being employed may be a copolymer in some cases. The repeat units forming the copolymer may be arranged in any fashion. For example, the repeat units may be arranged in a random order, in an alternating order, or as a block copolymer, i.e., comprising one or more regions each comprising a first repeat unit (e.g., a first block), and one or more regions each comprising a second repeat unit (e.g., a second block), etc. Block copolymers may have two (a diblock copolymer), three (a triblock copolymer), or more numbers of distinct blocks.

Disclosed particles can include copolymers, which, in some embodiments, describes two or more polymers (such as those described herein) that have been associated with each other, usually by covalent bonding of the two or more polymers together. Thus, a copolymer may comprise a first polymer and a second polymer, which have been conjugated together to form a block copolymer where the first polymer can be a first block of the block copolymer and the second polymer can be a second block of the block copolymer. Of course, those of ordinary skill in the art will understand that a block copolymer may, in some cases, contain multiple blocks of polymer, and that a "block copolymer," as used herein, is not limited to only block copolymers having only a single first block and a single second block. For instance, a block copolymer may comprise a first block comprising a first polymer, a second block comprising a second polymer, and a third block comprising a third polymer or the first polymer, etc. In some cases, block copolymers can contain any number of first blocks of a first polymer and second blocks of a second polymer (and in certain cases, third blocks, fourth blocks, etc.). In addition, it should be noted that block copolymers can also be formed, in some instances, from other block copolymers. For example, a first block copolymer may be conjugated to another polymer (which may be a homopolymer, a biopolymer, another block copolymer, etc.), to form a new block copolymer containing multiple types of blocks, and/or to other moieties (e.g., to non-polymeric moieties).

In some embodiments, the polymer (e.g., copolymer, e.g., block copolymer) can be amphiphilic, i.e., having a hydrophilic portion and a hydrophobic portion, or a relatively hydrophilic portion and a relatively hydrophobic portion. A hydrophilic polymer can be one generally that attracts water and a hydrophobic polymer can be one that generally repels water. A hydrophilic or a hydrophobic polymer can be identified, for example, by preparing a sample of the polymer and measuring its contact angle with water (typically, the polymer will have a contact angle of less than 60°, while a hydrophobic polymer will have a contact angle of greater than about) 60°. In some cases, the hydrophilicity of two or more polymers may be measured relative to each other, i.e., a first polymer may be more hydrophilic than a second polymer. For instance, the first polymer may have a smaller contact angle than the second polymer.

In one set of embodiments, a polymer (e.g., copolymer, e.g., block copolymer) contemplated herein includes a biocompatible polymer, i.e., the polymer that does not typically induce an adverse response when inserted or injected into a living subject, for example, without significant inflammation and/or acute rejection of the polymer by the immune system, for instance, via a T-cell response. Accordingly, the therapeutic particles contemplated herein can be non-immunogenic. The term non-immunogenic as used herein refers to endogenous growth factor in its native state which normally elicits no, or only minimal levels of, circulating antibodies, T-cells, or reactive immune cells, and which normally does not elicit in the individual an immune response against itself.

Biocompatibility typically refers to the acute rejection of material by at least a portion of the immune system, i.e., a nonbiocompatible material implanted into a subject provokes an immune response in the subject that can be severe enough such that the rejection of the material by the immune system cannot be adequately controlled, and often is of a degree such that the material must be removed from the subject. One simple test to determine biocompatibility can be to expose a polymer to cells in vitro; biocompatible polymers are polymers that typically will not result in significant cell death at moderate concentrations, e.g., at concentrations of 50 micrograms/$10^6$ cells. For instance, a biocompatible polymer may cause less than about 20% cell death when exposed to cells such as fibroblasts or epithelial cells, even if phagocytosed or otherwise uptaken by such cells. Non-limiting examples of biocompatible polymers that may be useful in various embodiments of the present invention include polydioxanone (PDO), polyhydroxyalkanoate, polyhydroxybutyrate, poly (glycerol sebacate), polyglycolide, polylactide, PLGA, polycaprolactone, or copolymers or derivatives including these and/or other polymers.

In certain embodiments, contemplated biocompatible polymers may be biodegradable, i.e., the polymer is able to degrade, chemically and/or biologically, within a physiological environment, such as within the body. As used herein, "biodegradable" polymers are those that, when introduced into cells, are broken down by the cellular machinery (biologically degradable) and/or by a chemical process, such as hydrolysis, (chemically degradable) into components that the cells can either reuse or dispose of without significant toxic effect on the cells. In one embodiment, the biodegradable polymer and their degradation byproducts can be biocompatible.

For instance, a contemplated polymer may be one that hydrolyzes spontaneously upon exposure to water (e.g., within a subject), the polymer may degrade upon exposure to heat (e.g., at temperatures of about 37° C.). Degradation of a polymer may occur at varying rates, depending on the polymer or copolymer used. For example, the half-life of the polymer (the time at which 50% of the polymer can be degraded into monomers and/or other nonpolymeric moieties) may be on the order of days, weeks, months, or years, depending on the polymer. The polymers may be biologically degraded, e.g., by enzymatic activity or cellular machinery, in some cases, for example, through exposure to a lysozyme (e.g., having relatively low pH). In some cases, the polymers may be broken down into monomers and/or other nonpolymeric moieties that cells can either reuse or dispose of without significant toxic effect on the cells (for example, polylactide may be hydrolyzed to form lactic acid, polyglycolide may be hydrolyzed to form glycolic acid, etc.).

In some embodiments, polymers may be polyesters, including copolymers comprising lactic acid and glycolic acid units, such as poly(lactic acid-co-glycolic acid) and poly(lactide-co-glycolide), collectively referred to herein as "PLGA"; and homopolymers comprising glycolic acid units, referred to herein as "PGA," and lactic acid units, such as poly-L-lactic acid, poly-D-lactic acid, poly-D,L-lactic acid, poly-L-lactide, poly-D-lactide, and poly-D,L-lactide, collectively referred to herein as "PLA." In some embodiments, exemplary polyesters include, for example, polyhydroxyacids; PEGylated polymers and copolymers of lactide and glycolide (e.g., PEGylated PLA, PEGylated PGA, PEGylated PLGA, and derivatives thereof. In some embodiments, polyesters include, for example, polyanhydrides, poly(ortho ester) PEGylated poly(ortho ester), poly(caprolactone), PEGylated poly(caprolactone), polylysine, PEGylated polylysine, poly(ethylene imine), PEGylated poly(ethylene imine), poly(L-lactide-co-L-lysine), poly(serine ester), poly (4-hydroxy-L-proline ester), poly[α-(4-aminobutyl)-L-glycolic acid], and derivatives thereof.

In some embodiments, a polymer may be PLGA. PLGA is a biocompatible and biodegradable co-polymer of lactic acid and glycolic acid, and various forms of PLGA can be characterized by the ratio of lactic acid:glycolic acid. Lactic acid can be L-lactic acid, D-lactic acid, or D,L-lactic acid. The degradation rate of PLGA can be adjusted by altering the lactic acid-glycolic acid ratio. In some embodiments, PLGA to be used in accordance with the present invention can be characterized by a lactic acid:glycolic acid ratio of approximately 85:15, approximately 75:25, approximately 60:40, approximately 50:50, approximately 40:60, approximately 25:75, or approximately 15:85.

In some embodiments, the ratio of lactic acid to glycolic acid monomers in the polymer of the particle (e.g., the PLGA block copolymer or PLGA-PEG block copolymer), may be selected to optimize for various parameters such as water uptake, therapeutic agent release and/or polymer degradation kinetics can be optimized.

In some embodiments, polymers may be one or more acrylic polymers. In certain embodiments, acrylic polymers include, for example, acrylic acid and methacrylic acid copolymers, methyl methacrylate copolymers, ethoxyethyl methacrylates, cyanoethyl methacrylate, amino alkyl methacrylate copolymer, poly(acrylic acid), poly(methacrylic acid), methacrylic acid alkylamide copolymer, poly(methyl methacrylate), poly(methacrylic acid polyacrylamide, amino alkyl methacrylate copolymer, glycidyl methacrylate copolymers, polycyanoacrylates, and combinations comprising one or more of the foregoing polymers. The acrylic polymer may comprise fully-polymerized copolymers of acrylic and methacrylic acid esters with a low content of quaternary ammonium groups.

In some embodiments, polymers can be cationic polymers. In general, cationic polymers are able to condense and/or protect negatively charged strands of nucleic acids (e.g. DNA, RNA, or derivatives thereof). Amine-containing polymers such as poly(lysine), polyethylene imine (PEI), and poly(amidoamine) dendrimers are contemplated for use, in some embodiments, in a disclosed particle.

In some embodiments, polymers can be degradable polyesters bearing cationic side chains. Examples of these polyesters include poly(L-lactide-co-L-lysine), poly(serine ester), poly(4-hydroxy-L-proline ester). A polymer (e.g., copolymer, e.g., block copolymer) containing poly(ethylene glycol) repeat units can also be referred to as a "PEGylated" polymer. Such polymers can control inflammation and/or immunogenicity (i.e., the ability to provoke an immune response) and/or lower the rate of clearance from the circulatory system via the reticuloendothelial system (RES), due to the presence of the poly(ethylene glycol) groups.

PEGylation may also be used, in some cases, to decrease charge interaction between a polymer and a biological moiety, e.g., by creating a hydrophilic layer on the surface of the polymer, which may shield the polymer from interacting with the biological moiety. In some cases, the addition of poly(ethylene glycol) repeat units may increase plasma half-life of the polymer (e.g., copolymer, e.g., block copolymer), for instance, by decreasing the uptake of the polymer by the phagocytic system while decreasing transfection/uptake efficiency by cells. Those of ordinary skill in the art will know of methods and techniques for PEGylating a polymer, for example, by using EDC (1-ethyl-3-(3-dimethylaminopropyl) carbodiimide hydrochloride) and NHS (N-hydroxysuccinimide) to react a polymer to a PEG group terminating in an amine, by ring opening polymerization techniques (ROMP), or the like.

Particles disclosed herein may or may not contain PEG. In addition, certain embodiments can be directed towards copolymers containing poly(ester-ether)s, e.g., polymers having repeat units joined by ester bonds (e.g., R—C(O)—O—R' bonds) and ether bonds (e.g., R—O—R' bonds). In some embodiments of the invention, a biodegradable polymer, such as a hydrolyzable polymer, containing carboxylic acid groups, may be conjugated with poly(ethylene glycol) repeat units to form a poly(ester-ether).

In one embodiment, the molecular weight of the polymers can be optimized for effective treatment as disclosed herein. For example, the molecular weight of a polymer may influence particle degradation rate (such as when the molecular weight of a biodegradable polymer can be adjusted), solubility, water uptake, and drug release kinetics. For example, the molecular weight of the polymer can be adjusted such that the particle biodegrades in the subject being treated within a reasonable period of time (ranging from a few hours to 1-2 weeks, 3-4 weeks, 5-6 weeks, 7-8 weeks, etc.). A disclosed particle can for example comprise a copolymer of PEG and PLGA, the PEG can have a molecular weight of 1,000-20,000, e.g., 5,000-20,000, e.g., 10,000-20,000, and the PLGA can have a molecular weight of 5,000-100,000, e.g., 20,000-70,000, e.g., 20,000-50,000.

In some embodiments, disclosed therapeutic particles and/or compositions include targeting agents such as dyes, for example Evans blue dye. Such dyes may be bound to or associated with a therapeutic particle, or disclosed compositions may include such dyes. For example, Evans blue dye may be used, which may bind or associate with albumin, e.g. plasma albumin.

Disclosed therapeutic particles, may, some embodiments, include a targeting moiety, i.e., a moiety able to bind to or otherwise associate with a biological entity, for example, a membrane component, a cell surface receptor, Her-2, the basement membrane of a blood vessel, basement membrane proteins, collagen, collagen IV or the like. For example, the targeting moiety can be a basement vascular membrane targeting peptide. The term "bind" or "binding," as used herein, refers to the interaction between a corresponding pair of molecules or portions thereof that exhibit mutual affinity or binding capacity, typically due to specific or non-specific binding or interaction, including, but not limited to, biochemical, physiological, and/or chemical interactions, disassociation constant).

For example, a targeting moiety may target tissue basement membrane, such as the basement membrane of a blood vessel. A "basement membrane" refers to a thin membrane upon which is posed about a single layer of cells. For example, a basement membrane can be made up of proteins held together by type IV collagen. Epithelial cells are anchored with hemidesmosome to the basement membrane. The end result resembles a layer of tiles attached to a thin sheet. In cases where the endothelium can be disrupted (by disease or trauma, e.g. the process of stent placement), the basement membrane may be exposed and accessible to particles.

In one embodiment, the targeting peptide included in a particle may have a length of at most 200 residues. In another embodiment, the targeting peptide or peptidomimetic portion of the particle can have a length of at most 50 residues. For example, a disclosed particle may include a targeting peptide or peptidomimetic that includes the amino acid sequence AKERC (SEQ ID NO: 3), CREKA (SEQ ID NO: 1), ARYLQKLN (SEQ ID NO: 4), CARYLQKLN (SEQ ID NO: 2) or AXYLZZLN (SEQ ID NO: 5), wherein X and Z can be variable amino acids, or conservative variants or peptidomimetics thereof. In some embodiments, the poly(amino acid) targeting moiety can be a peptide that includes the amino acid sequence AKERC (SEQ ID NO: 3), CREKA (SEQ ID NO: 1), ARYLQKLN (SEQ ID NO: 4) or AXYLZZLN (SEQ ID NO: 5), wherein X and Z can be variable amino acids, and can have a length of less than 20, 50 or 100 residues. Any peptide, or conservative variants or peptidomimetics thereof, that binds or forms a complex with collagen IV, or the basement membrane of a blood vessel, is contemplated for use as a targeting moiety.

In one embodiment, the targeting moiety can be an isolated peptide or peptidomimetic that can have a length of less than 100 residues and includes the amino acid sequence CREKA (Cys Arg Glu Lys Ala) (SEQ ID NO: 1) or a peptidomimetic thereof. Such an isolated peptide or peptidomimetic can have, for example, a length of less than 50 residues or a length of less than 20 residues. In some embodiments, the invention provides a peptide that includes the amino acid sequence CREKA (SEQ ID NO: 1) and can have a length of less than 20, 50 or 100 residues.

An exemplary embodiment includes a particle having a portion of the polymer matrix covalently bound to a peptide, such as the basement vascular membrane targeting peptide—e.g., a peptide may form a ligand on the polymer. Such covalent association may be through a linker, a polymer matrix can be covalently bound to the peptide via the free terminus of e.g., a PEG or e.g., can be covalently bound to the peptide via a carboxyl group at the free terminus of PEG. In another embodiment, the polymer matrix can be covalently bound to the peptide via a maleimide functional group at the free terminus of PEG.

In one embodiment, the ratio of peptide-bound polymer to free polymer can be selected to optimize the delivery and/or release of the anti-NIH agent to the basement vascular membrane of the blood vessel, or healing rate of the endothelial cells. For example, increased ligand density (e.g., on a PLGA-PEG copolymer) may increase target binding (cell binding/target uptake). Alternatively, a certain concentration of non-functionalized polymer (e.g., non functionalized PLGA-PEG copolymer) in the therapeutic particle may control inflammation and/or immunogenicity (i.e., the ability to provoke an immune response), may allow a particle to have a circulation half-life that can be therapeutically effective for the treatment of NIH. Furthermore, a non-functionalized polymer may lower the rate of clearance from the circulatory system via the reticuloendothelial system. For example, a non-functionalized polymer may balance an otherwise high concentration of peptides, which can otherwise accelerate clearance by the subject, resulting in less delivery to the target cells.

The anti-NIH agent may be associated with the surface of, encapsulated within, surrounded by, and/or dispersed throughout the therapeutic particle. In another embodiment, the anti-NIH agent can be encapsulated within the therapeutic particle.

Therapeutic compositions disclosed herein may, for example, be locally administered to a designated region of the blood vessel where the NIH occurs. In still another embodiment, the therapeutic composition can be administered via a medical device. In yet another embodiment, the medical device can be a drug eluding stent, needle catheter, or stent graft. In one embodiment, the therapeutic compositions of this invention pass through the endothelial layer of a blood vessel due to plaque damage of the endothelial tissue and bind to collagen IV of the basement membrane.

For example, contemplated particles may include CREKA bound to PEG (CREKA-PEG (SEQ ID NO: 6)), CREKA bound to PEG that is bound to a lipid (SEQ ID NO: 7) (e.g., CREKA-PEGDSPE (SEQ ID NO: 8)), and CREKA bound to PEG-PLGA (CREKA-PEG-PLGA (SEQ ID NO: 9)). Exemplary particles may include a compound such as Formula VI and/or Formula VII:

be in the cis conformation. In some embodiments, a double bond of an unsaturated fatty acid may be in the trans conformation.

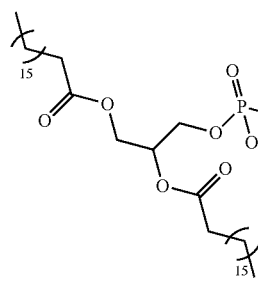
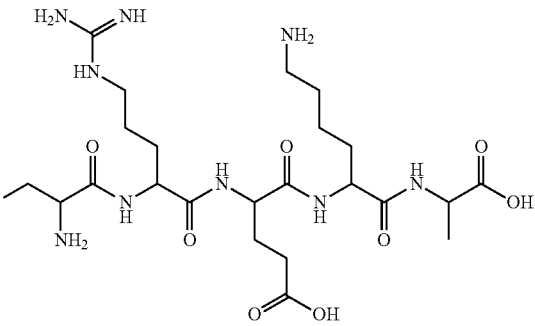

(SEQ ID NO: 10)

wherein n is 20 to 1720; and

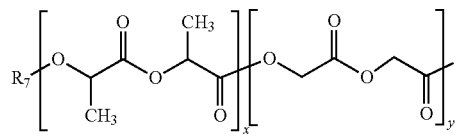
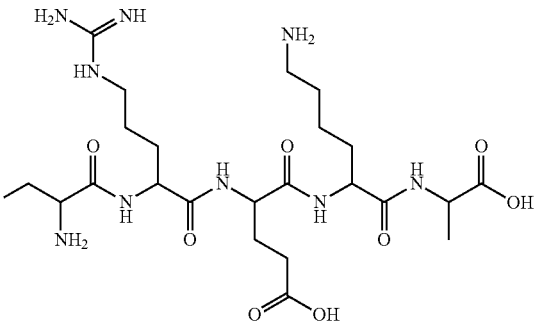

(SEQ ID NO: 11)

wherein $R_7$ is an alkyl group or H, $R_8$ is an ester or amide linkage, X+Y=20 to 1720, and Z=25 to 455. In other embodiments, X=0 to 1 mole fraction Y=0 to 0.5 mole fraction.

In certain embodiments, the polymers of a disclosed particle may be conjugated to a lipid. The polymer may be, for example, a lipid-terminated PEG. As described below, the lipid portion of the polymer can be used for self assembly with another polymer, facilitating the formation of a particle. For example, a hydrophilic polymer could be conjugated to a lipid that will self assemble with a hydrophobic polymer.

In some embodiments, lipids can be oils. In general, any oil known in the art can be conjugated to the polymers used in the invention. In some embodiments, an oil may comprise one or more fatty acid groups or salts thereof. In some embodiments, a fatty acid group may comprise digestible, long chain (e.g., $C_8$-$C_{50}$), substituted or unsubstituted hydrocarbons. In some embodiments, a fatty acid group may be a $C_{10}$-$C_{20}$ fatty acid or salt thereof. In some embodiments, a fatty acid group may be a $C_{15}$-$C_{20}$ fatty acid or salt thereof. In some embodiments, a fatty acid may be unsaturated. In some embodiments, a fatty acid group may be monounsaturated. In some embodiments, a fatty acid group may be polyunsaturated. In some embodiments, a double bond of an unsaturated fatty acid group may In some embodiments, a fatty acid group may be one or more of butyric, caproic, caprylic, capric, lauric, myristic, palmitic, stearic, arachidic, behenic, or lignoceric acid. In some embodiments, a fatty acid group may be one or more of palmitoleic, oleic, vaccenic, linoleic, alpha-linolenic, gamma-linoleic, arachidonic, gadoleic, arachidonic, eicosapentaenoic, docosahexaenoic, or erucic acid.

In another embodiment, a disclosed particle can be associated with (e.g., surrounded by) a small molecule amphiphilic compound e.g. having as possible components: 1) a biodegradable polymeric material that forms the core of the particle, which can carry bioactive drugs and release them at a sustained rate after cutaneous, subcutaneous, mucosal, intramuscular, ocular, systemic, oral or pulmonary administration; 2) a small molecule amphiphilic compound that surrounds the polymeric material forming a shell for the particle; and 3) a targeting molecule that can bind to a unique molecular signature on cells, tissues, or organs of the body, such as the basement vascular membrane.

For example, a targeting molecule can be first chemically conjugated to the hydrophilic region of a small molecule amphiphilic compound. This conjugate can be then mixed with a certain ratio of unconjugated small molecule amphiphilic compounds in an aqueous solution containing one or more water-miscible solvents. In one embodiment, the targeting molecule can be one or a plurality of peptides, small molecules, or combinations thereof. The amphiphilic compound can be, but is not limited to, one or a plurality of the following: naturally derived lipids, surfactants, or synthesized compounds with both hydrophilic and hydrophobic moieties. The water miscible solvent can be, but is not limited to: acetone, ethanol, methanol, and isopropyl alcohol. Separately, a biodegradable polymeric material can be mixed with the agent or agents to be encapsulated in a water miscible or partially water miscible organic solvent. In one embodiment, the biodegradable polymer can be any of the biodegradable polymers disclosed herein, for example, poly(D,L-lactic acid), poly(D,L-glycolic acid), poly(ε-caprolactone), or their copolymers at various molar ratios. The carried agent can be, but is not limited to, one or a plurality of the following therapeutic agents discussed below, including, for example, therapeutic drugs, imaging probes, or hydrophobic or lipophobic molecules for medical use. The water miscible organic solvent can be but is not limited to: acetone, ethanol, methanol, or isopropyl alcohol. The partially water miscible organic solvent can be, but is not limited to: acetonitrile, tetrahydrofuran, ethyl acetate, isopropyl alcohol, isopropyl acetate, or dimethylformamide. The resulting polymer solution can then added to the aqueous solution of conjugated and unconjugated amphiphilic compound to yield particles by the rapid diffusion of the organic solvent into the water and evaporation of the organic solvent.

Contemplated herein are particles that include surface modification, e.g. to enhance arterial uptake. Such surface modifying agents include for example heparin, L-R-phosphatidylethanolamine, cyanoacrylate, epoxide, fibronectin, fibrinogen, ferritin, lipofectin, didodecyldimethylammonium bromide, and DEAEDextran, and any other surface modifying agent disclosed in J Pharm Sci. 1998 October; 87(10): 1229-34, which is incorporated herein by reference in it entirety.

Polymer particles having more than one polymer or macromolecule present, and libraries involving such polymers or macromolecules are contemplated herein. For example, in one set of embodiments, particles may contain more than one distinguishable polymers (e.g., copolymers, e.g., block copolymers), and the ratios of the two (or more) polymers may be independently controlled, which allows for the control of properties of the particle. For instance, a first polymer may be a polymeric conjugate comprising a targeting moiety and a biocompatible portion, and a second polymer may comprise a biocompatible portion but not contain the targeting moiety, or the second polymer may contain a distinguishable biocompatible portion from the first polymer. Control of the amounts of these polymers within the polymeric particle may thus be used to control various physical, biological, or chemical properties of the particle, for instance, the size of the particle (e.g., by varying the molecular weights of one or both polymers), the surface charge (e.g., by controlling the ratios of the polymers if the polymers have different charges or terminal groups), the surface hydrophilicity (e.g., if the polymers have different molecular weights and/or hydrophilicities), the surface density of the targeting moiety (e.g., by controlling the ratios of the two or more polymers), etc.

As a specific example, a particle may comprise a first polymer comprising a poly(ethylene glycol) and a targeting moiety conjugated to the poly(ethylene glycol), and a second polymer comprising the poly(ethylene glycol) but not the targeting moiety, or comprising both the poly(ethylene glycol) and the targeting moiety, where the poly(ethylene glycol) of the second polymer can have a different length (or number of repeat units) than the poly(ethylene glycol) of the first polymer. As another example, a particle may comprise a first polymer comprising a first biocompatible portion and a targeting moiety, and a second polymer comprising a second biocompatible portion different from the first biocompatible portion (e.g., having a different composition, a substantially different number of repeat units, etc.) and the targeting moiety. As yet another example, a first polymer may comprise a biocompatible portion and a first targeting moiety, and a second polymer may comprise a biocompatible portion and a second targeting moiety different from the first targeting moiety.

In some cases, the particle can be a nanoparticle, i.e., the particle can have a characteristic dimension of less than about 1 micrometer, where the characteristic dimension of a particle is the diameter of a perfect sphere having the same volume as the particle. For example, a particle may have a characteristic dimension of the particle that may be less than about 300 nm, less than about 200 nm, less than about 150 nm, less than about 100 nm, less than about 50 nm, less than about 30 nm, less than about 10 nm, less than about 3 nm, or less than about 1 nm in some cases. In some embodiments, a disclosed particle may have a diameter of 50 nm-200 nm.

In general, the particles disclosed herein can be about 40 nm to about 500 nm in size, for example, may be less than or equal to about 90 nm in size, e.g., about 40 nm to about 80 nm, e.g., about 40 nm to about 60 nm. For example, particles less than about 90 nm in size, may reduce liver uptake by the subject, and may thereby allow longer circulation in the bloodstream.

In an embodiment, particles disclosed herein may have a surface zeta potential ranging from about −80 mV to 50 mV. Zeta potential is a measurement of surface potential of a particle. In some embodiments, the particles can have a zeta potential ranging between 0 mV and −50 mV, e.g., between −1 mV and 50 mV. In some embodiments, the particles can have a zeta potential ranging between −1 mV and −25 mV. In some embodiments, the particles can have a zeta potential ranging between −1.1 mV and −10 mV.

In other embodiments, the particles disclosed herein can include liposomes, liposome polymer combinations, dendrimers, and albumin particles that can be functionalized with a peptide ligand.

A polymeric conjugate to be used in the preparation of disclosed particle may be formed using any suitable conjugation technique. For instance, two components such as a targeting moiety and a biocompatible polymer, a biocompatible polymer and a poly(ethylene glycol), etc., may be conjugated together using techniques such as EDC-NHS chemistry (1-ethyl-3-(3-dimethylaminopropyl) carbodiimide hydrochloride and N-hydroxysuccinimide) or a reaction involving a maleimide or a carboxylic acid, which can be conjugated to one end of a thiol, an amine, or a similarly functionalized polyether. In another set of embodiments, a conjugation reaction may be performed by reacting a polymer that comprises a carboxylic acid functional group (e.g., a poly(ester ether) compound) with a polymer or other moiety (such as a targeting moiety) comprising an amine. For instance, a targeting moiety, such as a poly(amino-acid) ligand, may be reacted with an amine to form an amine-containing moiety, which can then be conjugated to the carboxylic acid of the polymer. Such a reaction may occur as a single-step reaction, i.e., the conjugation can be performed without using intermediates such as N-hydroxysuccinimide or a maleimide.

For example, provided herein is a method of preparing therapeutic particles, comprising: a) providing an anti-NIH agent; b) providing at least one polymer; optionally c) providing a basement vascular membrane targeting peptide; d) mixing the at least one polymer with the anti-NIH agent to prepare particles; and optionally e) associating the particles with the basement vascular membrane targeting peptide; such that the therapeutic particles are formed. For example, at least one polymer can be a copolymer of two or more polymers, such as PLGA and PEG. Also provided herein is a method of preparing therapeutic particles comprising: a) providing an anti-NIH agent; b) providing a first polymer; c) providing a second, non-functionalized polymer; optionally d) providing a basement vascular membrane targeting peptide; e) reacting the first polymer with the peptide to prepare a peptide-bound polymer; and f) mixing the peptide-bound polymer with the second, non-functionalized polymer and the anti-NIH agent; such that the therapeutic particles are formed.

Disclosed particles and/or compositions may be delivered to a blood vessel using a medical device such as a needle catheter, irrigation catheter, balloon catheter, or can be delivered via intravenously e.g., by i.v. infusion. In an exemplary embodiment, a balloon catheter, (e.g. the Genie™ balloon catheter available from Acrostak) and may be inserted into a vessel having a lesion and in need of a stent. The balloon can be inflated to provide a pre-dilation of the vessel. The therapeutic composition can be, for example, then delivered to the blood vessel, followed by insertion of a bare metal stent, or the stent may be placed first and the composition then delivered.

Particles may be delivered to a subject in need thereof using delivery devices that have been developed for endovascular local gene transfer such as passive diffusion devices (e.g., double-occlusion balloon, spiral balloon), pressure-driven diffusion devices (e.g., microporous balloon, balloon-in-balloon devices, double-layer channeled perfusion balloon devices, infusion-sleeve catheters, hydrogel-coated balloons), and mechanically or electrically enhanced devices (e.g., needle injection catheter, iontophoretic electric current-enhanced balloons, stent-based system), or any other delivery system disclosed in Radiology 2003; 228:36-49, or Int J Nanomedicine 2007; 2(2):143-61, which are incorporated herein by reference in their entirety.

For example, as shown in FIG. 1A, a diagnostic/irrigation catheter 30 is used to deliver the therapeutic composition 40 to a blood vessel 10, such that the delivery of the therapeutic particles is in the blood flow 20. In an exemplary different delivery method (FIG. 1B), a balloon catheter 60 may be inserted into a blood vessel 10 with the blood flow 20, proximal to the target delivery site. The balloon is inflated, preventing blood flow into area 50 of the blood vessel 10, then the therapeutic composition 40 is injected into the catheter 60, thus localizing its delivery, with proximal landing of the particles. Alternatively, a diagnostic/irrigation catheter 30 may be used that includes balloon catheter 60 fed through it (FIG. 1C). The diagnostic/irrigation catheter 30 is inserted into the blood vessel 10 proximal to the target delivery site. The balloon catheter 60 is then fed to a site 50 distal to the target delivery site. The balloon is inflated to prevent blood flow 20, then the therapeutic composition 40 is introduced via the diagnostic/irrigation catheter, such that the delivery is distal. An exemplary optional delivery method may include a first balloon catheter fed through a second balloon catheter. The first balloon catheter, proximal to the target delivery site, is inflated, followed by inflation of the second balloon catheter that has been fed to a position distal to the target delivery site. The therapeutic composition is introduced via the first balloon catheter such that it is trapped between the two balloons, e.g. includes both distal and proximal delivery.

In some embodiments, disclosed compositions may be administered intravenously, e.g., systemically. For example, provided herein is a method of preventing or deterring NIH in a blood vessel of a patient receiving a bare metal stent in a lesion of said blood vessel, comprising intravenously administering a composition that includes therapeutic particles, wherein said therapeutic particles comprise a basement vascular membrane targeting peptide and an anti-NIH agent. Such therapeutic particles may substantially localize in the blood vessel e.g, that receives the bare metal stent. In some embodiments, intravenous administration may result in blood vessel localization comparable to or more substantially as compared to administration of disclosed compositions using e.g. a guide catheter and/or an angioplasty balloon.

As described above, disclosed compositions may provide a decreased or substantially comparable restenosis or NIH rate in the patient after receiving the vascular stent as compared to the restenosis rate obtained by administration of a vascular stent, e.g. a bare metal stent alone. NIH or restenosis may be measured in angiographically (e.g, with binary restenosis), or clinically (e.g., target lesion revascularization). Binary restenosis, or angiographic restenosis, may include 50% or more diameter stenosis (DS) at follow up. It can be measured either by visual inspection or by quantitative coronary angiography (QCA). The percent of binary restenosis may correlate directly with lesion length; vessel diameter; and/or the presence of diabetes. Target Lesion Revascularization (TLR) usually includes a need for a repeat intervention at the site of the lesion due to the recurrence of symptoms. It is a clinical way to measure restenosis, although it can occur for reasons other than restenosis, such as disease progression or a new lesion adjacent to the original treated area. Late loss studies may also be conducted and late loss may be independent of vessel size. Calculation of late loss may allow the level of restenosis to be accounted for in all vessels, regardless of size. Unlike binary restenosis, late loss does not allow a narrowed vessel of any magnitude to go undetected. Late loss is measured in millimeters. The equation for this process is: Minimum Lumen Diameter (MLD) Post Procedure−MLD Follow-up=Late Loss.

The present disclosure also provides pharmaceutical compositions comprising particles as disclosed herein formulated together with one or more pharmaceutically acceptable carriers. Exemplary materials which can serve as pharmaceutically acceptable carriers include, but are not limited to, sugars such as lactose, glucose, and sucrose; starches such as corn starch and potato starch; cellulose and its derivatives such as sodium carboxymethyl cellulose, ethyl cellulose, and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols such as propylene glycol; esters such as ethyl oleate and ethyllaurate; agar; detergents such as TWEEN™ 80; buffering agents such as magnesium hydroxide and aluminum hydroxide; alginic acid; pyrogen-free water; isotonic saline; Ringer's solution; ethyl alcohol; and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator. If filtration or other terminal sterilization methods are not feasible, the formulations can be manufactured under aseptic conditions.

The pharmaceutical compositions of this invention can be administered to a patient by any means known in the art including oral and parenteral routes, and/or systemically, e.g., by IV infusion or injection. In one embodiment, the disclosed particles may be administered by IV infusion. In one embodiment, disclosed particles may be locally administered, for example, brought into contact with the blood vessel wall or vascular tissue through a device.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension, or emulsion in a nontoxic parenterally acceptable diluent or solvent, for example, as a solution in 1,3-butanediol. Among the acceptable vehicles and solvents that may be employed are water, Ringer's solution, U.S.P., and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid can be used in the preparation of injectables. In one embodiment, the inventive conjugate is suspended in a carrier fluid comprising 1% (w/v) sodium carboxymethyl cellulose and 0.1% (v/v) TWEEN™ 80. The injectable formulations can be sterilized, for example, by filtration through a bacteria-retaining filter, or by incorporating sterilizing agents in the form of sterile solid compositions which can be dissolved or dispersed in sterile water or other sterile injectable medium prior to use.

Therapeutic particles disclosed herein may be formulated in dosage unit form for ease of administration and uniformity of dosage. The expression "dosage unit form" as used herein refers to a physically discrete unit of particle appropriate for the patient to be treated. It will be understood, however, that the total daily usage of the compositions of the present invention will be decided by the attending physician within the scope of sound medical judgment. For any particle, the therapeutically effective dose can be estimated initially either in cell culture assays or in animal models, usually mice, rabbits, dogs, or pigs. The animal model can be also used to achieve a desirable concentration range and route of administration. Such information can then be used to determine useful doses and routes for administration in humans. Therapeutic efficacy and toxicity of particles can be determined by standard pharmaceutical procedures in cell cultures or experimental animals, e.g., $ED_{50}$ (the dose is therapeutically effective in 50% of the population) and $LD_{50}$ (the dose is lethal to 50% of the population). The dose ratio of toxic to therapeutic effects is the therapeutic index, and it can be expressed as the ratio, $LD_{50}/ED_{50}$. Pharmaceutical compositions which exhibit large therapeutic indices may be useful in some embodiments. The data obtained from cell culture assays and animal studies can be used in formulating a range of dosage for human use.

Also provided herein are kits that include a disclosed composition and a stent, optionally with instructions for administering any of the compositions described herein by any suitable technique as previously described, for example, orally, intravenously, pump or implantable delivery device, or via another known route of drug delivery.

EXAMPLES

Example 1

Simulation of Delivery of Therapeutic Particles

A balloon catheter is inserted into a length of 3.1 mm Tygon tubing. Water is injected at the opposite end at physiological blood pressure, 2 psi (103 mmHg). This water is dyed blue in order to ascertain whether the balloon would withstand physiological pressure once inflated. A three way valve with syrine is used for injection of a green solution to inflate the balloon and a second syringe to pull vacuum. A valve with syringe attached is used for injection of a blue solution through a lumen to distal end of balloon. After infusion of 0.3 mL of blue solution, the pressure inside the tube is about 4 psi (206 mmHg), which is higher than healthy human blood pressure, and the balloon withstands pressure with no leakage downstream.

Example 2

Tissue Binding and Persistence of Nanoparticle Formulation in Denuded Rabbit Iliac Arteries 16 New Zealand white rabbits were used. Animals were kept in accordance with Institutional Animal Care and Use Committee (IACUC) protocols. To prevent or reduce the occurrence of thrombotic events, animals were treated with acetylsalicylic acid (40 mg, per os [PO]) daily, at least one day prior to the beginning of the study. Animals were anesthetized according to the testing facility standard operating procedures. After induction of anesthesia, the left or right carotid artery was accessed with an incision made in the throat region. An arterial sheath was introduced and advanced into the artery. As an anti-coagulation therapy, an initial bolus of heparin (~70 IU/kg) was given following cannulation of the carotid artery.

Before the first angiogram, 1 mL of nitroglycerine (0.5 mg/mL) IV was given. The iliac artery was circumscribed (from the femoral to the internal iliac branch) and Quantitative Angiography (QA) was performed to document the vessel size. Then, balloon injury was performed in both iliac arteries of each rabbit. The appropriate balloon (balloon to artery ratio of 1.3:1 or more if needed) was advanced over the guidewire to traverse the distal portion of the pre-selected injury site. The inflated balloon was then retracted from the femoral artery back into the aorta to enable denudation of the target vasculature. The balloon was deflated and re-advanced to traverse the target injury site. The balloon was deflated while it was in the terminal descending aorta and the denudation procedure repeated one more time (total of 3 times). A post-denudation angiogram was performed and TIMI flow was assessed. An animal with post-TIMI flow of 0 or 1 received an intra-arterial infusion of nitroglycerine at the discretion of the interventionalist to restore the flow to 2 or 3. The guide wire was then advanced to the opposite iliac artery, and the injury procedure was repeated with the appropriate sized balloon for the second artery.

PLA-PEG-lipid-CREKA (SEQ ID NO: 1) nanoparticles with a diameter of ~240 nm and labeled with a fluorescent tag were administered with a particle dye load of about 1 wt. %. The targeted nanoparticles had a concentration of 6 mg/ml in the administered composition before 50% dilution with contrast media. Animals were dosed with 3 mL of 6 mg/mL nanoparticles in 50% contrast media such that for local delivery, 3 mL of solution were delivered to each iliac artery (resulting in 18 mg dose of nanoparticles delivered to all animals).

Four methods were used for delivery of the nanoparticles: guide catheter, angioplasty balloon, guide catheter and angioplasty balloon, and systemic i.v. Four animals received the nanoparticle solution by each of the four methods. For each method, two animals were sacrificed within 30 minutes of delivery ("acute") and the other two animals were sacrificed 24 hours after delivery. In acute cases of local delivery, 5-15 minutes elapsed between injury and delivery, and 5 minutes elapsed between delivery and sacrifice. For acute i.v. administration, an hour elapsed between delivery and sacrifice.

Guide catheter: After both arteries had been balloon denuded, the guide catheter was advanced over the guidewire near the delivery site. Two milliliters of the nanoparticle formulation combined with an appropriate amount of contrast agent (1 mL) for a total delivery volume of 3 mL was administered in one minute via the guide catheter locally to the site of balloon injury. This procedure was repeated for the other injured iliac artery.

Angioplasty balloon: After both arteries had been balloon denuded, the guidewire was removed. The balloon was then inflated sufficiently to occlude blood flow in the iliac artery. Two milliliters of the nanoparticle formulation mixed with an appropriate amount of contrast agent (1 mL) for a total delivery volume of 3 mL was administered via the lumen of the balloon catheter while the artery was occluded over a period of one minute. The balloon was then deflated, retracted, and advanced over the guidewire to the other iliac artery. The delivery procedure was repeated in the second artery.

Guide catheter with angioplasty balloon: After both arteries had been balloon denuded, a 5F guide catheter was advanced to the first iliac artery. An angioplasty balloon was then advanced through the guide catheter to the delivery site, approximately 1-2 cm distally from the tip of the guide catheter. The balloon was inflated sufficiently to occlude blood flow in the iliac artery. Two milliliters of the nanoparticle formulation mixed with an appropriate amount of contrast agent (1 mL) for a total delivery volume of 3 mL was then administered via the guide catheter while the artery was occluded over a period of approximately one minute. The balloon was then deflated, and both the balloon and guide catheter were retracted, and advanced to the other iliac artery. The delivery procedure was repeated in the second artery.

Systemic i.v.: Immediately after balloon denudation, the animals received a single i.v. injection of 2 mL of nanoparticle formulation combined with 1 mL of saline for a total delivery volume of 3 mL, in the same volume ratio as the nanoparticle formulations with contrast for the other delivery methods. Injection was at the marginal vein of the ear.

Upon completion of nanoparticle delivery to the second iliac artery in animals from the acute cohort, with the exception of the systemic i.v. delivery group, the animals were kept deeply anesthetised before euthanasia with a rapid bolus of pentobarbital. This bolus was administered within 30 minutes after delivery.

Animals from the 24 hour cohort, as well as from the systemic i.v. delivery group, were allowed to regain consciousness. At the appropriate sacrifice time (1 hour after nanoparticle delivery for the acute systemic i.v. group, or 24 hours after nanoparticle delivery for all the 24 hour groups), the animals were first tranquilized with acepromazine administered sub-cutaneously [SC]. Heparin (~70 IU/kg) was administered prior to sacrifice for the 24 hour groups only. The animals were then euthanized with a rapid bolus of pentobarbital.

After euthanasia, the soft tissue surrounding the external iliac arteries was dissected off gently to expose the external artery wall, from about 1 cm proximal to the internal iliac branch to about 1 cm distal to the femoral branch. Between these two branches, a central 2 cm long segment was delimited (in the delivery region), using a dot of black ink at the proximal end and a dot of red ink at the distal end. The ink was allowed to dry, then the artery was explanted, by cutting it from about 1 cm proximal to the internal iliac branch to about 1 cm distal to the femoral branch. The explanted segment was gently rinsed by immersion in approximately 10 milliliters of physiologic saline. Excess saline was gently removed from the explanted iliac vessels by gentle padding on absorbent paper.

The explanted segments were then sectioned and embedded in an OCT (optimal cutting temperature) cryomold. After freezing in liquid nitrogen, the arteries were cut into 10 sections each, resulting in 320 sections from 16 animals having 2 iliac arteries each. The sections were mounted on slides and viewed at 10× magnification for lumen detail and 4× magnification for the whole section. The segments were scored on a scale of 0-3 for the amount of fluorescence observed above tissue background, with 0 being no fluorescence, 1 very few points of fluorescence, 2 many points of fluorescence, and 3 being a continuous layer of fluorescence. A total of 1800 images were collected and 1630 were scored. Table 1 provides the average score for each delivery method at the acute and 24 hour time points.

TABLE 1

| Delivery Mode | Delivery Location | Average Score - Acute - Animals 1 and 2 | Average Score - 24 hour - Animals 1 and 2 |
|---|---|---|---|
| Guide Catheter | Local | 1.8 | 0.08 |
|  |  | 2.1 | 0.00 |
| Angioplasty Balloon | Local | 1.9 | 0.09 |
|  |  | 1.7 | 0.04 |
| Guide Catheter with Angioplasty Balloon | Local | 1.1 | 0.13 |
|  |  | 2.2 | 0.12 |
| i.v. | Systemic | 2.5 | 0.07 |
|  |  | 2.2 | 0.02 |

Of the images, 33 were identified as having good fluorescence results. Twenty of these images were from the systemic i.v. group, 6 were from the guide catheter group, 4 were from the guide catheter with angioplasty balloon group, and 3 were from the angioplasty balloon group. These results illustrate the effectiveness of systemic i.v. delivery to target nanoparticles of the invention to a site of arterial injury.

Example 3

General Synthetic Procedure for Particles

Product constituents were dissolved in organic solvent system (generally 79% ethyl acetate, 21% benzyl alcohol) at a given solids concentration (generally 15% w/w). This organic phase was emulsified with a rotor stator homogenizer with aqueous phase pre-saturated with solvent (generally 2% benzyl alcohol, 4% ethyl acetate, and sometimes with sodium cholate included as a surfactant). The weight ratio of aqueous:organic was commonly 10:1. This emulsion was formed into a fine emulsion though high pressure homogenization on a microfluidizer (generally microfluidics 110S air driven homogenizer, processing pressure ~9000 psi). The emulsion was quenched into a cold water quench, generally at 10:1 quench:emulsion ratio. Polysorbate-20 (T-20) was added to the quench to solubilize unencapsulated drug. The slurry was then processed with ultrafiltration/diafiltration to remove T-20 and unencapsulated drug. Solids and drug assays were performed on the final slurry to determine drug loading. In order to provide freeze-thaw stability, the final slurries were brought to 10% sucrose (w/w) then stored frozen.

Example 4

Particles with placebo containing ~10 kDa PLA and 5% DSPE-PEG5k were prepared using the procedure of Example 3. No surfactant was used and the particle size after 3 passes on the homogenizer was 153.5 nm.

Example 5

Effect of Lipid Content on Particle Size

Figure 2:
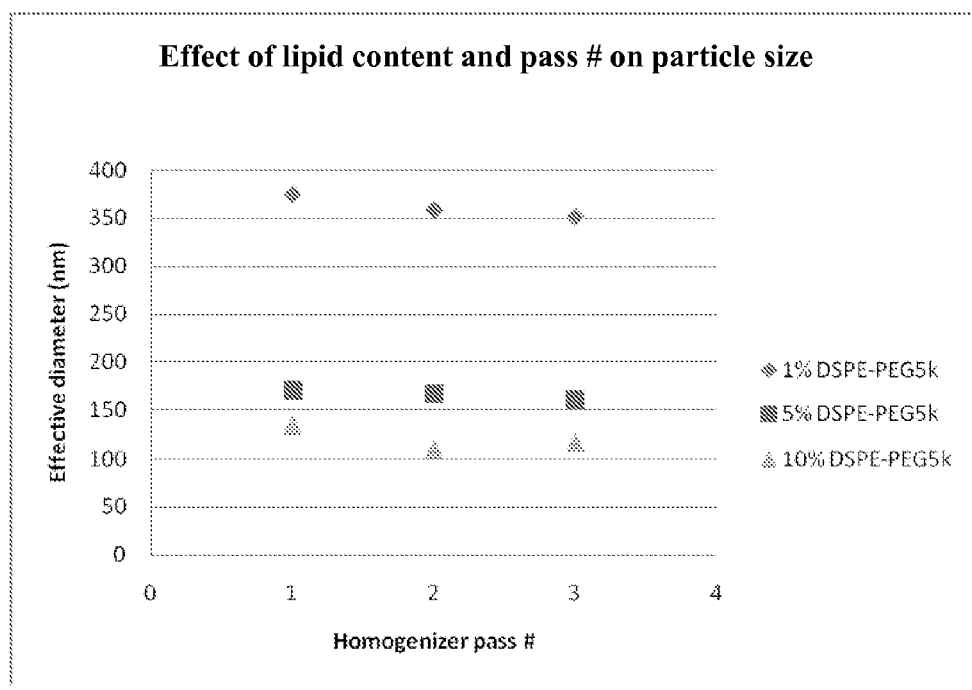
FIG. 2 depicts the effect of lipid content and number of homogenizer passes on particle size using DSPE-PEG5K.

DSPE-PEG5k at 1%, 5%, and 10% of solids were prepared as in Example 2 using PLA ~10 kDa and the effect on particle size was investigated. Additional PEG-lipid decreased the particle size, as shown in FIG. 2.

Figure 3:
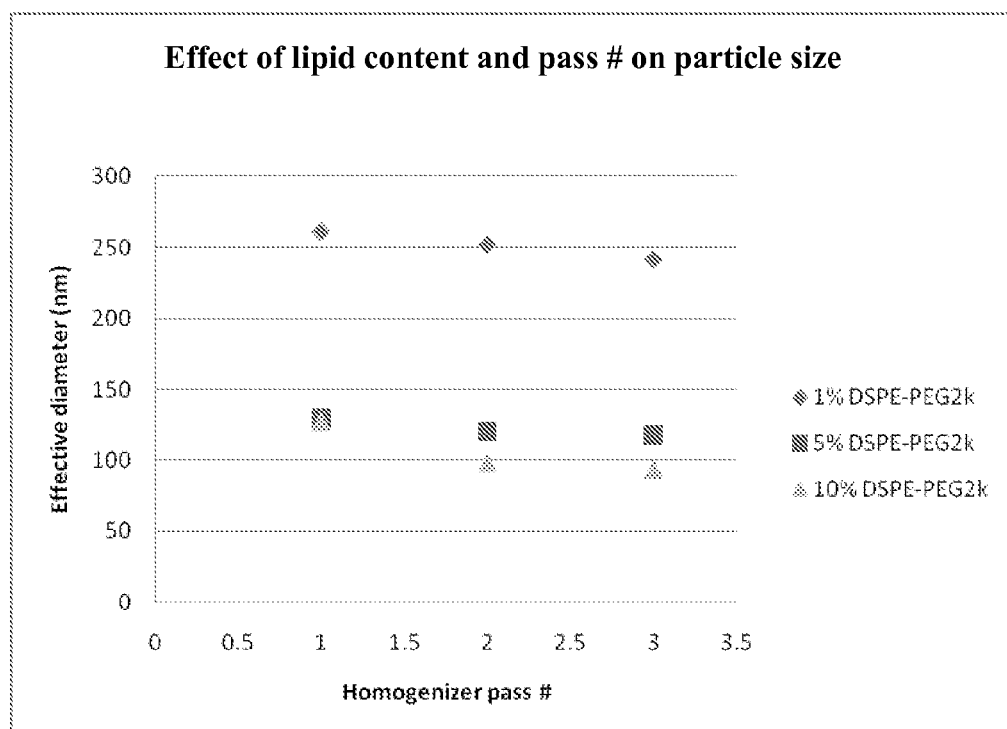
FIG. 3 depicts the effect of lipid content and number of homogenizer passes on particle size using DSPE-PEG5K.

Shorter 2 kDa PEG chains on the lipid, DSPE-PEG2k, were also investigated for effect on particle size using DSPE-PEG2k at 1%, 5%, and 10% of solids. The PLA used was ~10 kDa. The particle size, shown in FIG. 3, was reduced relative to the above, which used DSPE-PEG5k. This may be because the shorter PEG chain may give the PEG-lipid better surfactant qualities. Further, the shorter PEG chain may mean that at a given wt % PEG-lipid, there is a greater number of PEG-lipids present when the PEG chain is shorter.

Example 6

Paclitaxel Release

Particles with PTXL (paclitaxel) incorporated at a target load of 20%, with 5% DSPE-PEG5k were prepared as in Example 2 (Lot 126) The PLA used was ~10 kDa. The final particle size was 174.7 nm, and the PTXL load was 16.1%.

Figure 4:
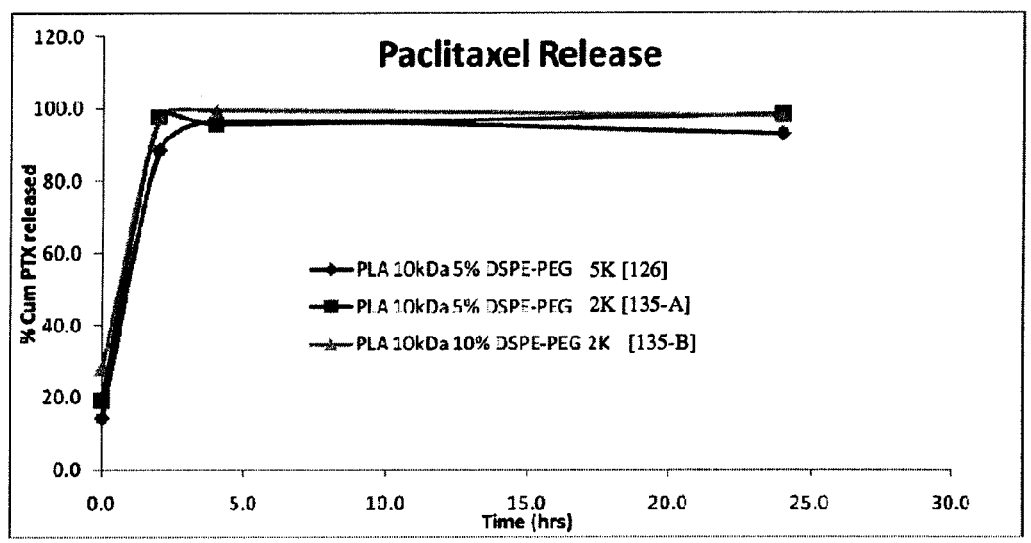
FIG. 4 depicts release of paclitaxel loaded particles at 37° C.

Lots with PTXL incorporated at a target load of 20% were also prepared with 5% (Lot 135A) or 10% (135B) DSPE-PEG2k. The PLA used was ~10 kDa. The final particle size was 133.2 nm (A) and 94.2 nm (B), and the PTXL was 15.1% (A) and 13.1% (B). This indicates good encapsulation is still achieved, even with particles under 100 nm. Release testing at 37° C. on these particles is shown in FIG. 4.

Example 7

Paclitaxel Release

PTXL was incorporated into particles containing 16.5/5 PLA/PEG copolymer using the procedure of Example 3. The final particle size was 85 nm and the PTXL load was 6.6%. The particle size was slightly smaller than the target of ~100 nm (Lot 148)

Lot 152 was prepared by incorporating PTXL at a target load of 20%, with 5% DSPE-PEG5k, and high MW PLA, ~85 kDa. The final particle size was 242.8 nm, and the PTXL load was 17.2%.

Lot 156(A) was prepared by incorporating PTXL at a target load of 20%, with 5% DSPE-PEG2k, using PLA with ~22 kDa. The particle size was 133.9 nm and 15.2% drug load.

Lot 156(A) was prepared by incorporating PTXL at a target load of 20%, with no PEG-lipid, using ~10 KDa PLA.

Figure 5:
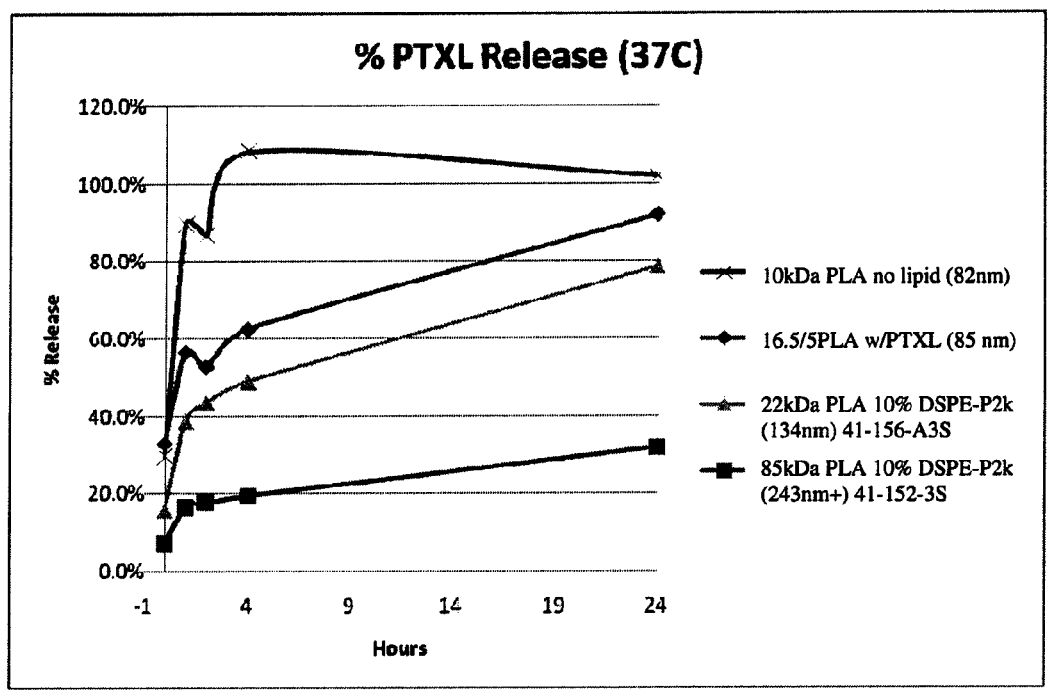
FIG. 5 depicts release of various paclitaxel loaded particles at 37° C.

The release testing, shown in FIG. 5, indicates that the cause of the fast release appears to be the low MW (~10 kDa) PLA. High MW (~85 kDa) PLA exhibited significantly slower release. This suggests that the release can be altered through the use of higher MW PLAs. It is possible the large particle size played a role in decreasing the release, but previous work has shown little dependence of release on particle size.

Example 8

Paclitaxel Release

Lot 41-191 incorporated PTXL at a target load of 20%, with 10% DSPE-PEG2k, 20% Alexa fluor 647-PLA, and ~22 kDa PLA. The final particle size was 135.2 nm, and the PTXL load was 16.8%. This is the non-targeted material for CV-INVIV-003. Alexa fluor 647-PLA is incorporated so that arteries can be assessed with fluorescence microscopy to assess particle binding.

For lot 41-205, PTXL was incorporated at a target load of 20%, with ~10% DSPE-PEG2k, 20% Alexa fluor 647-PLA, ~22 kDa PLA, and 5 mol % of either DSPE-PEG2k-CREKA (SEQ ID NO: 12) (41-205(A)) or DSPE-PEG2k-CARYLQKLN (SEQ ID NO: 13) (41-205(B)). The final particle size was 122.8 nm (A) and 145.1 nm (B), and the PTXL load was 14.9% (A) and 16.2% (B). These are the targeted PEG-lipid formulations in CV-INVIV-003.

Figure 6:
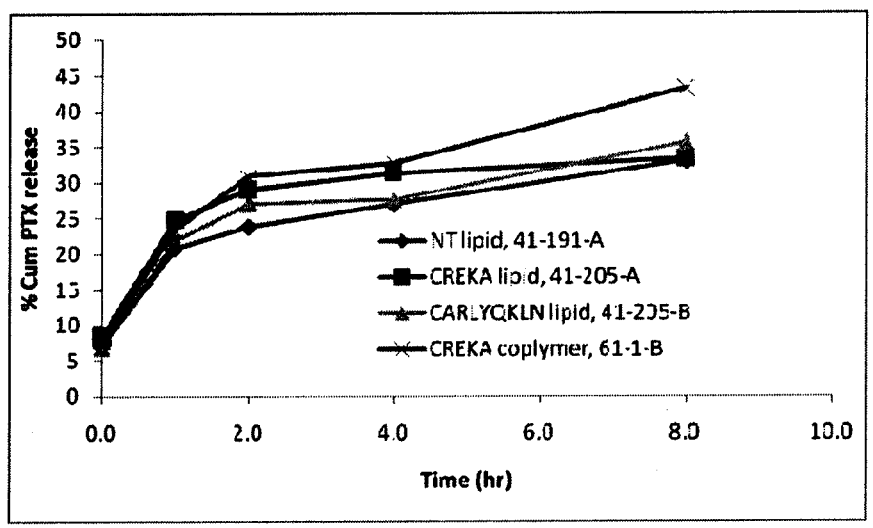
FIG. 6 depicts release of various paclitaxel loaded particles.

Lot 61-1 incorporated PTXL at a target load of 20%, with 20% Alexa fluor 647-PLA, 10 mol % PLA-PEG-CREKA, with 16.5/5 PLA/PEG. The final particle size was 103.5 nm, and the PTXL load was 14.2%. This is the copolymer targeted material for CV-INVIV-003. Release profiles are shown in FIG. 6.

Example 9

Animal Model—Dosing with Paclitaxel

Rabbits were used as in Example 2. One femoral artery in anesthetized rabbits was denuded with a balloon injury model. Briefly, a balloon catheter was overinflated ~30% then pulled along the artery three times, intended to injure the artery and effectively remove the endothelial cells. The animals were then dosed with a solution of a given formulation, at 1 mg/kg PTXL, including abraxane. Abraxane is PTXL in an albumin nanoparticulate formulation, which rapidly dissolved upon administration, mimicking free drug.

Figure 7:
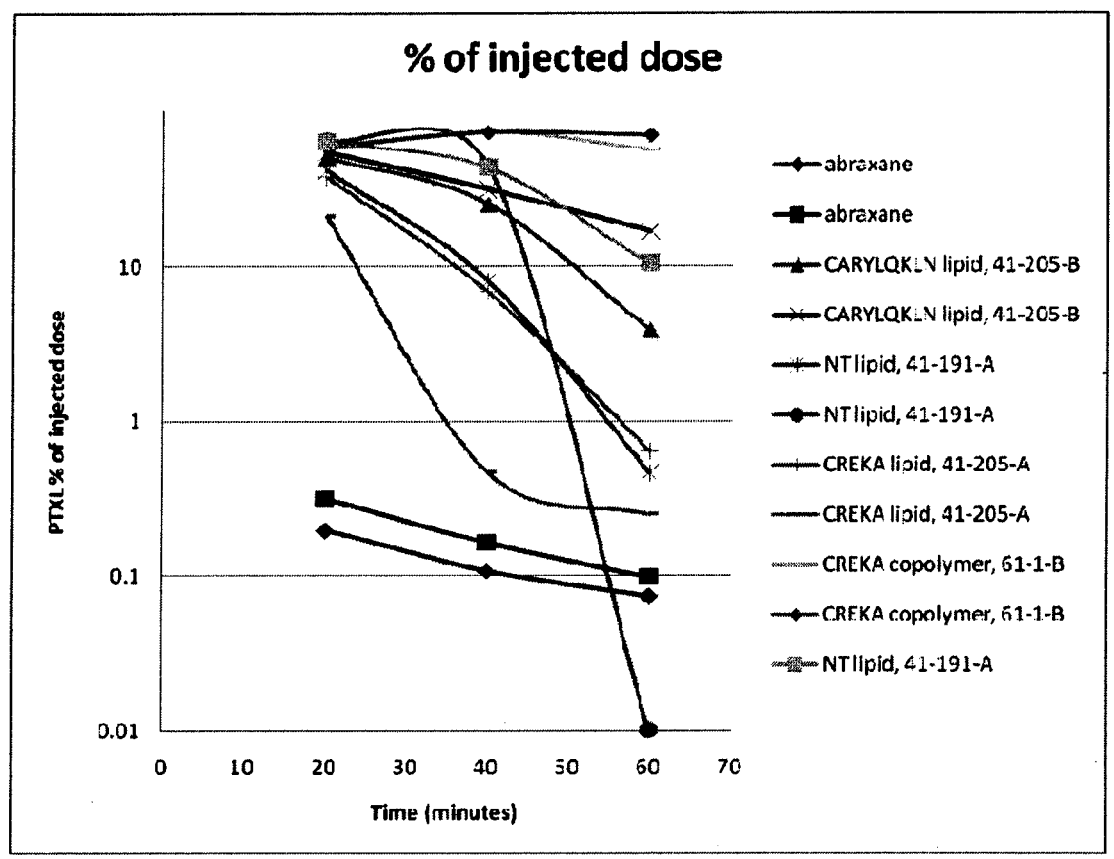
FIG. 7 depicts pharmacokinetics of various paclitaxel loaded particles in a rabbit model.

Blood was drawn from the animal at 20, 40 and 60 minutes, at which time they were sacrificed. As the release profiles of all formulations were very similar, any significant differences in the plasma profiles likely indicate altered particle circulation times/clearance. The data shown in FIG. 7 indicates that the longest circulating particles are those of the copolymer, while the lipid particle formulations appear to have a faster clearance rate. However all formulations do successfully exhibit prolonged circulation times, as free drug is rapidly cleared from the plasma, as modeled in the abraxane arms.

Example 10

Paclitaxel Dosing Via IV in Animal Model

Rabbits were used as in Example 2 Paclitaxel loaded particles were administered to rabbit injured vessels via IV injection. Each animal had one iliac artery injured via balloon expansion while the other artery was undisturbed. Nanoparticles were injected in the marginal ear vein immediately after injury and blood drawn every 20 minutes to monitor paclitaxel blood levels. The animals were sacrificed after 60 minutes and vessels removed to measure their Paclitaxel content.

Multiple particles were tested including non-targeted lipid based particles, targeted lipid based particles, and targeted copolymer based particles. Table 2 lists the formulation details for the particles tested. Ligands were either attached to the DSPE-PEG lipids or PLA-PEG copolymers, as described above, depending on the formulation.

TABLE 2

| | Nanoparticle | Targeting ligand | Payload | PTXL Loading (%) | Particle Size (nm) |
|---|---|---|---|---|---|
| 1 | lipid | CREKA (SEQ ID NO: 1) | PTXL | 15 | 123 |
| 2 | lipid | CARYLQKLN (SEQ ID NO: 2) | PTXL | 16 | 145 |
| 3 | lipid | none | PTXL | 17 | 135 |
| 4 | copolymer | CREKA (SEQ ID NO: 1) | PTXL | 14 | 104 |
| 5 | N/A | N/A | Albumin-bound paclitaxel | 10 | ~130 |

Figure 8:
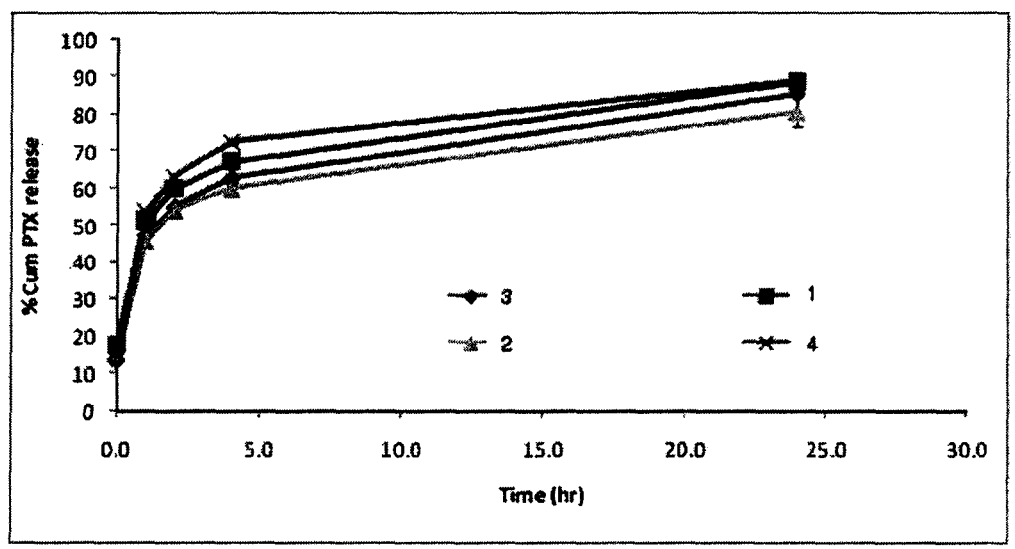
FIG. 8 depicts the paclitaxel release rate of disclosed nanoparticles with paclitaxel, in a rabbit model.
Figure 9:
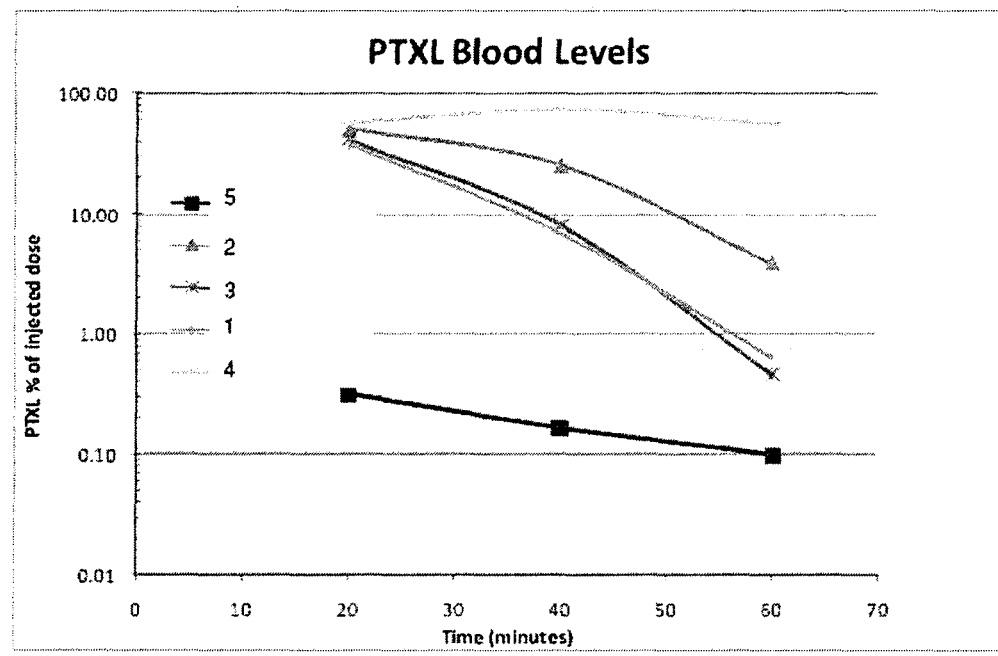
FIG. 9 depicts the paclitaxel blood levels in a disclosed rabbit model.

Release rate from formulations 1 through 4 are shown in FIG. 8. The nanoparticles had similar release rates in an in vitro release assay which should allow comparisons between the different formulations in the animals. Blood levels are shown in FIG. 9. The copolymer (formulation 4) had sustained blood concentration compared to the albumin paclitaxel and lipid based nanoparticles.

Figure 10:
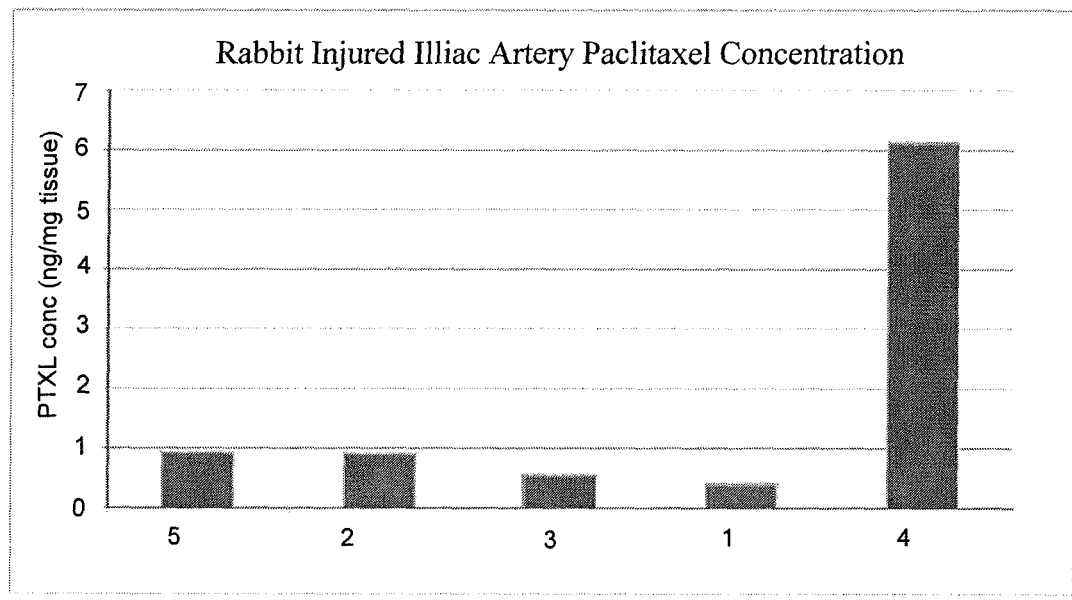
FIG. 10 depicts injured artery paclitaxel concentration in a rabbit model, after administration of disclosed nanoparticles having paclitaxel.

FIG. 10 indicates vessel levels. The copolymer had significantly higher tissue levels than other formulations.

Equivalents

While specific embodiments of the subject invention have been discussed, the above specification is illustrative and not restrictive. Many variations of the invention will become apparent to those skilled in the art upon review of this specification. The full scope of the invention should be determined by reference to the claims, along with their full scope of equivalents, and the specification, along with such variations.

Unless otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in this specification and attached claims are approximations that may vary depending upon the desired properties sought to be obtained by the present invention.

What is claimed is:

1. A therapeutic particle comprising:
   about 1 to about 20 mole percent PLA-PEG-basement vascular membrane targeting peptide, wherein the targeting peptide comprises PLA having a number average molecular weight of about 15 to about 20 kDa and PEG having a number average molecular weight of about 4 to about 6 kDa;
   about 10 to about 25 weight percent anti-neointimal hyperplasia (NIH) agent; and
   about 50 to about 90 weight percent non-targeted poly-lactic acid-PEG, wherein the therapeutic particle is capable of releasing the anti-NIH agent to a basement vascular membrane of a blood vessel for at least about 8 hours when the therapeutic particle is placed in the blood vessel.

2. The therapeutic particle of claim 1, wherein the non-targeted poly-lactic acid-PEG has PLA with a number average molecular weight of about 20 kDa to about 25 kDa.

3. The therapeutic particle of claim 2, wherein the basement vascular membrane targeting peptide is selected from: CREKA (SEQ ID NO: 1) or CARLYQKLN (SEQ ID NO: 2).

4. The therapeutic particle of claim 3, wherein the anti-neointimal hyperplasia (NIH) agent is paclitaxel.

* * * * *

UNITED STATES PATENT AND TRADEMARK OFFICE
CERTIFICATE OF CORRECTION

| | | |
|---|---|---|
| PATENT NO. | : 8,563,041 B2 | Page 1 of 1 |
| APPLICATION NO. | : 12/636105 | |
| DATED | : October 22, 2013 | |
| INVENTOR(S) | : Amy Grayson et al. | |

It is certified that error appears in the above-identified patent and that said Letters Patent is hereby corrected as shown below:

In the Claims

At column 32, claim number 4, line number 18, please delete "claim 3" and insert -- claim 2 -- in its place.

Signed and Sealed this
Twenty-ninth Day of March, 2016

Michelle K. Lee
*Director of the United States Patent and Trademark Office*

SEQUENCE LISTING

<160> NUMBER OF SEQ ID NOS: 13

<210> SEQ ID NO 1
<211> LENGTH: 5
<212> TYPE: PRT
<213> ORGANISM: Artificial Sequence
<220> FEATURE:
<223> OTHER INFORMATION: Synthetic Peptide

<400> SEQUENCE: 1

Cys Arg Glu Lys Ala
1               5

<210> SEQ ID NO 2
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 2

Cys Ala Arg Leu Tyr Gln Lys Leu Asn
1               5

<210> SEQ ID NO 3
<211> LENGTH: 5
<212> TYPE: PRT
<213> ORGANISM: Artificial Sequence
<220> FEATURE:
<223> OTHER INFORMATION: Synthetic Peptide

<400> SEQUENCE: 3

Ala Lys Glu Arg Cys
1               5

<210> SEQ ID NO 4
<211> LENGTH: 8
<212> TYPE: PRT
<213> ORGANISM: Artificial Sequence
<220> FEATURE:
<223> OTHER INFORMATION: Synthetic Peptide

```
<400> SEQUENCE: 4

Ala Arg Tyr Leu Gln Lys Leu Asn
1               5

<210> SEQ ID NO 5
<211> LENGTH: 8
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (2)..(2)
<223> OTHER INFORMATION: Xaa at position 2 may be a variable amino acid
<220> FEATURE:
<221> NAME/KEY: MISC_FEATURE
<222> LOCATION: (5)..(6)
<223> OTHER INFORMATION: Xaa at positions 5 and 6 may be variable amino
      acids

<400> SEQUENCE: 5

Ala Xaa Tyr Leu Xaa Xaa Leu Asn
1               5

<210> SEQ ID NO 6
<211> LENGTH: 5
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<223> OTHER INFORMATION: Covalent bond to PEG

<400> SEQUENCE: 6

Cys Arg Glu Lys Ala
1               5

<210> SEQ ID NO 7
<211> LENGTH: 5
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<223> OTHER INFORMATION: Covalent bond to PEG that is covalently bonded
      to a lipid

<400> SEQUENCE: 7

Cys Arg Glu Lys Ala
1               5

<210> SEQ ID NO 8
<211> LENGTH: 5
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<223> OTHER INFORMATION: Covalent bond to PEG that is covalently bonded
      to DSPE

<400> SEQUENCE: 8

Cys Arg Glu Lys Ala
1               5
```

```
<210> SEQ ID NO 9
<211> LENGTH: 5
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<223> OTHER INFORMATION: Covalent bond to PEG that is covalently bonded
      to PLGA

<400> SEQUENCE: 9

Cys Arg Glu Lys Ala
1               5

<210> SEQ ID NO 10
<211> LENGTH: 5
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(1)
<223> OTHER INFORMATION: PEG is covalently bonded to the thiol group of
      cysteine, DSPE is covalently bonded to PEG

<400> SEQUENCE: 10

Cys Arg Glu Lys Ala
1               5

<210> SEQ ID NO 11
<211> LENGTH: 5
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(1)
<223> OTHER INFORMATION: PEG is covalently bonded to the thiol group of
      cysteine, PLGA is covalently bonded to PEG

<400> SEQUENCE: 11

Cys Arg Glu Lys Ala
1               5

<210> SEQ ID NO 12
<211> LENGTH: 5
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<223> OTHER INFORMATION: Covalent bond to PEG2k that is covalently
      bonded to DSPE

<400> SEQUENCE: 12

Cys Arg Glu Lys Ala
1               5

<210> SEQ ID NO 13
<211> LENGTH: 9
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<223> OTHER INFORMATION: Covalent bond to PEG2k that is covalently
      bonded to DSPE
```

-continued

```
<400> SEQUENCE: 13

Cys Ala Arg Tyr Leu Gln Lys Leu Asn
1               5
```